United States Patent [19]
Wang et al.

[11] Patent Number: 5,681,940
[45] Date of Patent: Oct. 28, 1997

[54] SUGAR MODIFIED NUCLEOSIDES AND OLIGONUCLEOTIDES

[75] Inventors: Guangyi Wang, Irvine; Kandasamy Ramasamy, Laguna Hills; Wilfried E. Seifert, La Jolla, all of Calif.

[73] Assignee: ICN Pharmaceuticals, Costa Mesa, Calif.

[21] Appl. No.: 333,545

[22] Filed: Nov. 2, 1994

[51] Int. Cl.$^6$ .............. C07H 19/00; C07H 21/02; C07H 21/00; A01N 43/04

[52] U.S. Cl. .............. 536/22.1; 536/23.1; 536/25.3; 514/44

[58] Field of Search .............. 514/44; 536/22.1, 536/23.1, 25.3

[56] References Cited

U.S. PATENT DOCUMENTS 5,446,137 8/1995 Maag et al. .............. 536/23.1

OTHER PUBLICATIONS

Rabow L. and Stubbe, J., "Identification of the Alkaline–Labile Product Accompanying Cytosine Release during Bleomycin–Mediated Degradation of d(CGCGCG)", *J. Am. Chem. Soc.* 1986, 108, 7130–7131 (dated 1986).

*Primary Examiner*—Ardin H. Marschel
*Assistant Examiner*—Jezia Riley
*Attorney, Agent, or Firm*—Crockett & Fish

[57] ABSTRACT

A number of modified nucleosides are disclosed composed of modified sugar moieties which contain substituents at C1 and C4 positions, or branched substituents at C3 and C5 positions of deoxyribose or ribose. Each nucleoside is converted to or properly protected and then converted to the corresponding phosphoramidites. These phosphoramidites are used to assemble oligonucleotides in which there is at least one forenoted nucleosides. These sugar modified oligonucleotides have the potential to be used as antisense therapies since they are expected to enhance nuclease resistance and cellular uptake while they maintain sequence-specificity and affinity to nucleic acid targets in vitro or in vivo.

9 Claims, 8 Drawing Sheets

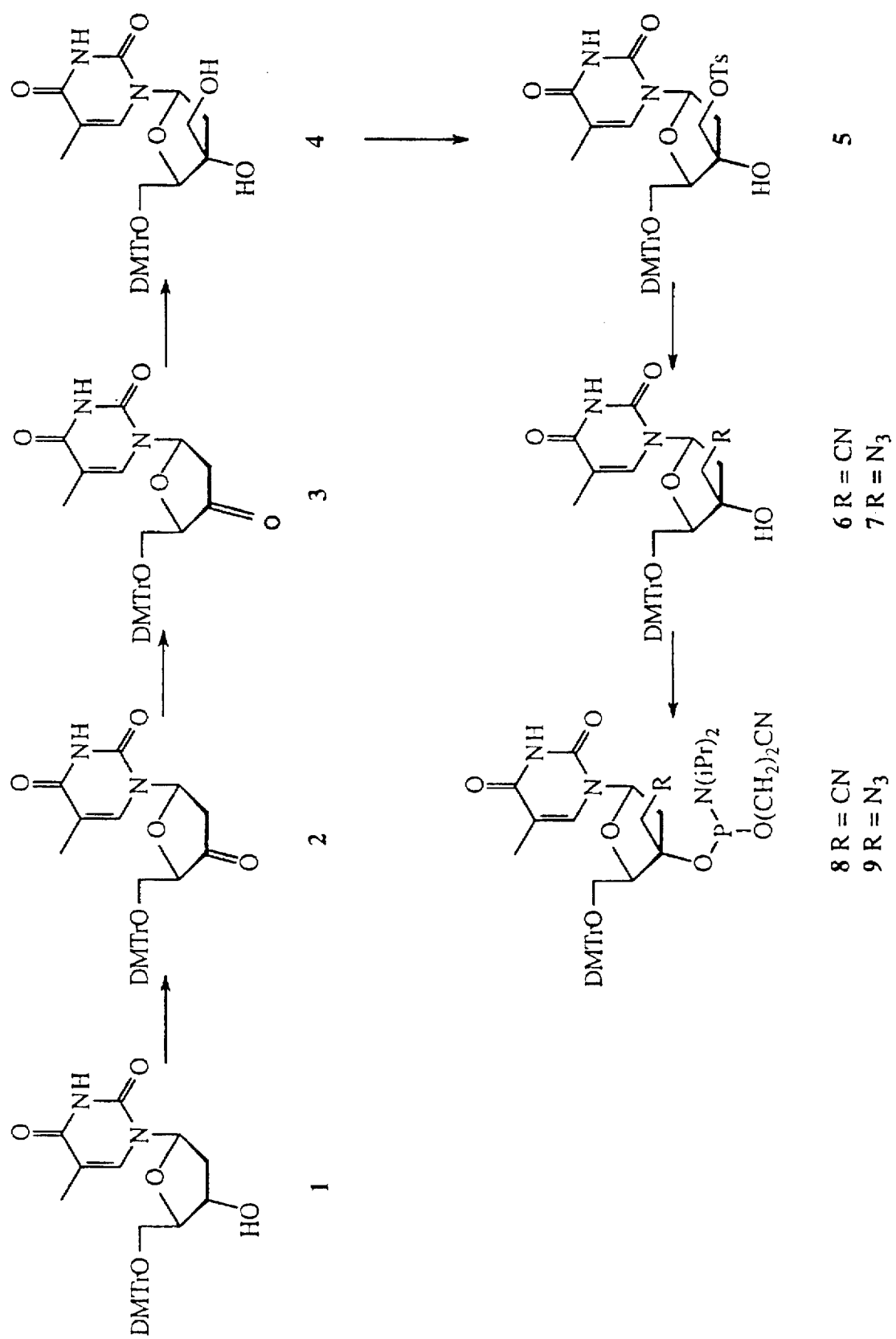

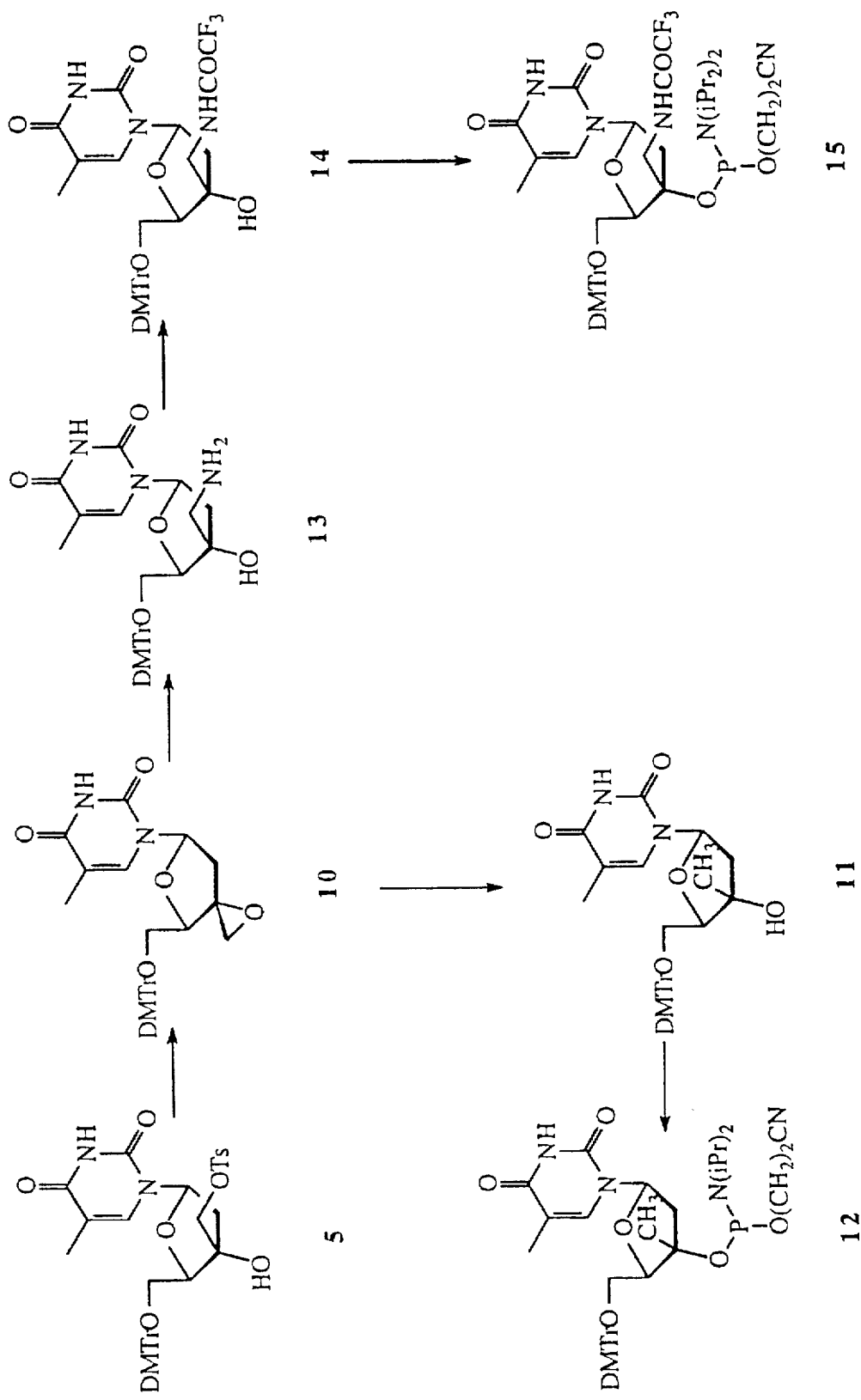
Figure 3. Reaction scheme 2.

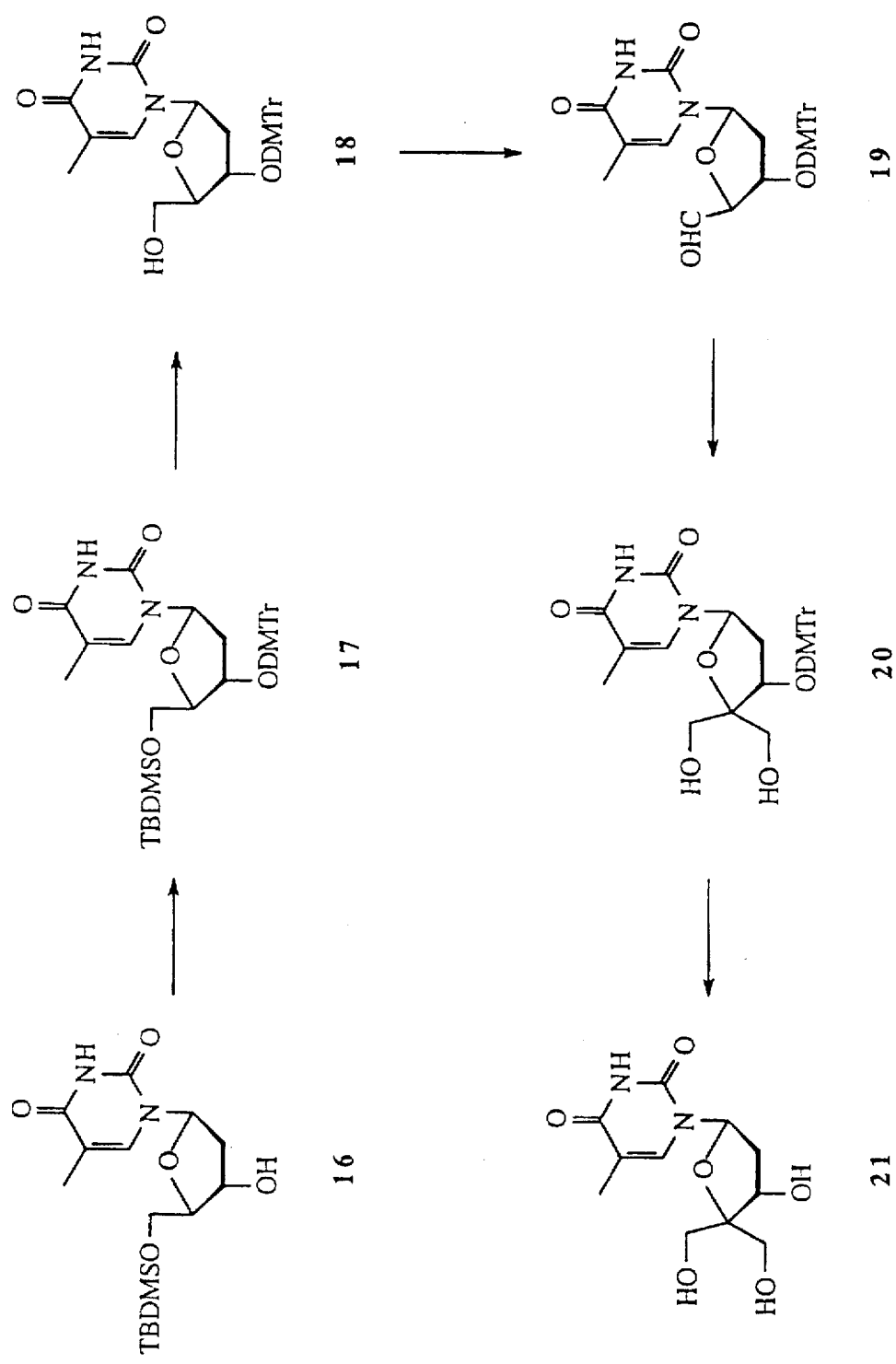
Figure 4. Reaction scheme 3.

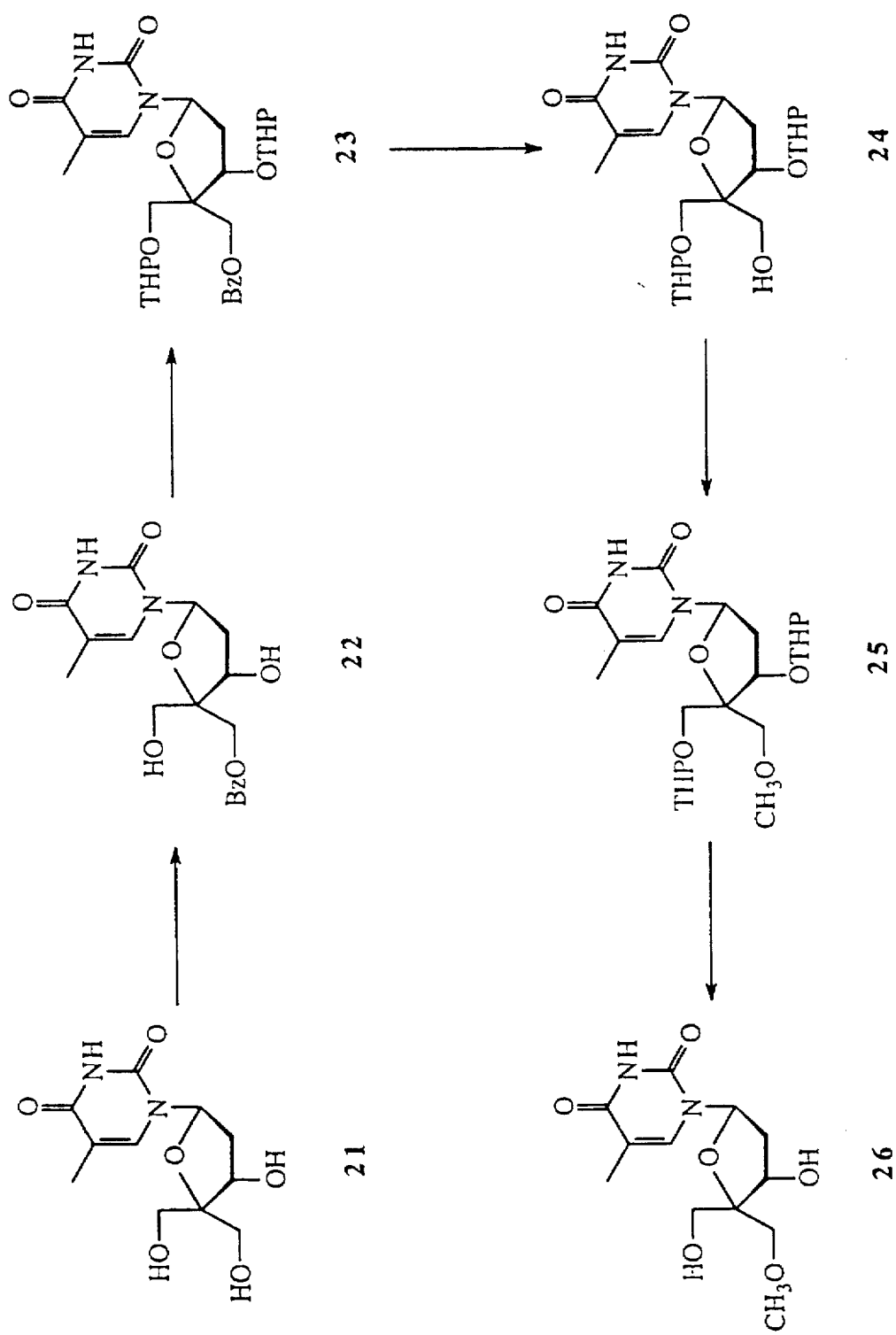
Figure 5. Reaction scheme 3 (Cont'd).

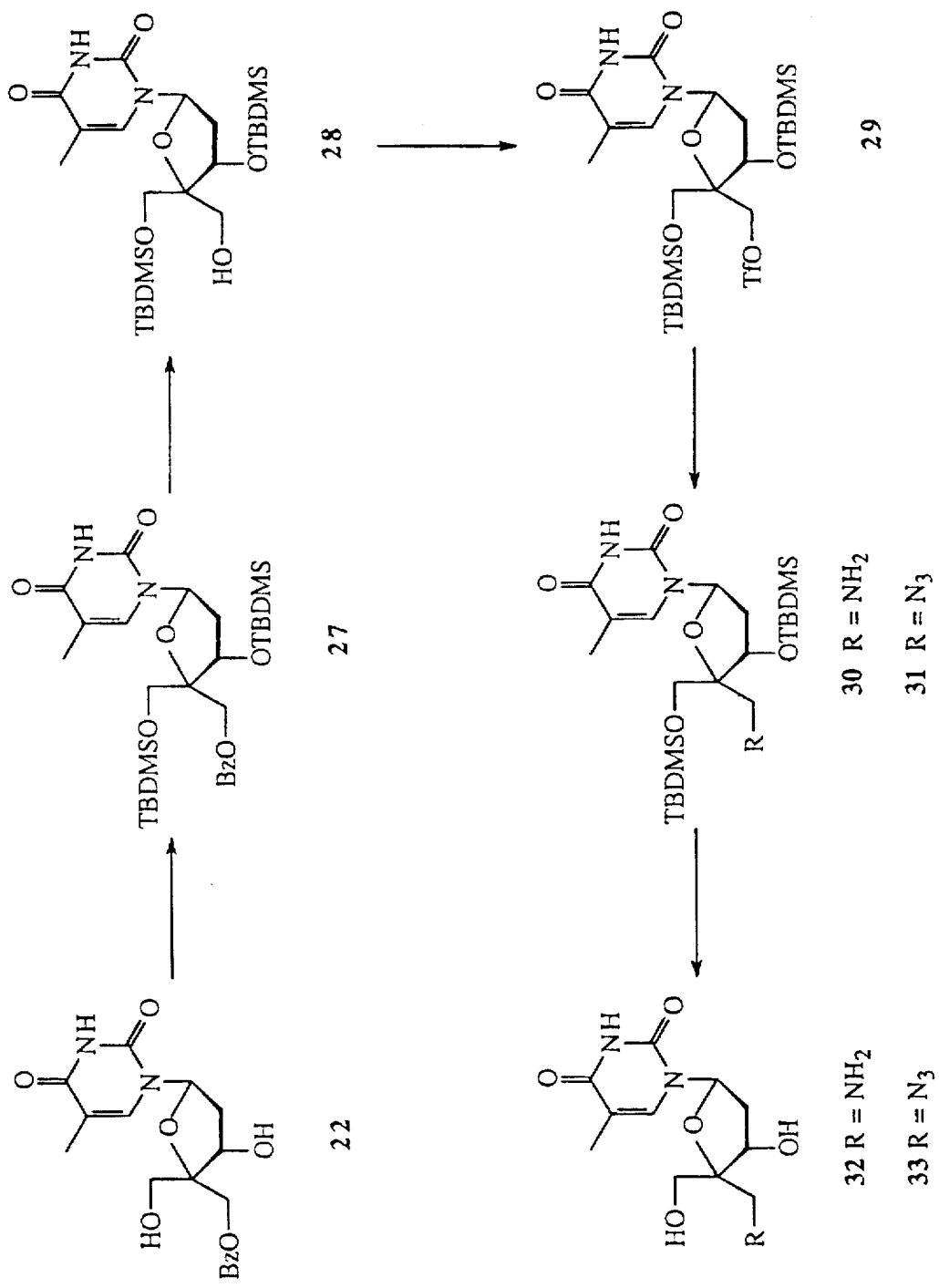
Figure 6. Reaction scheme 4.

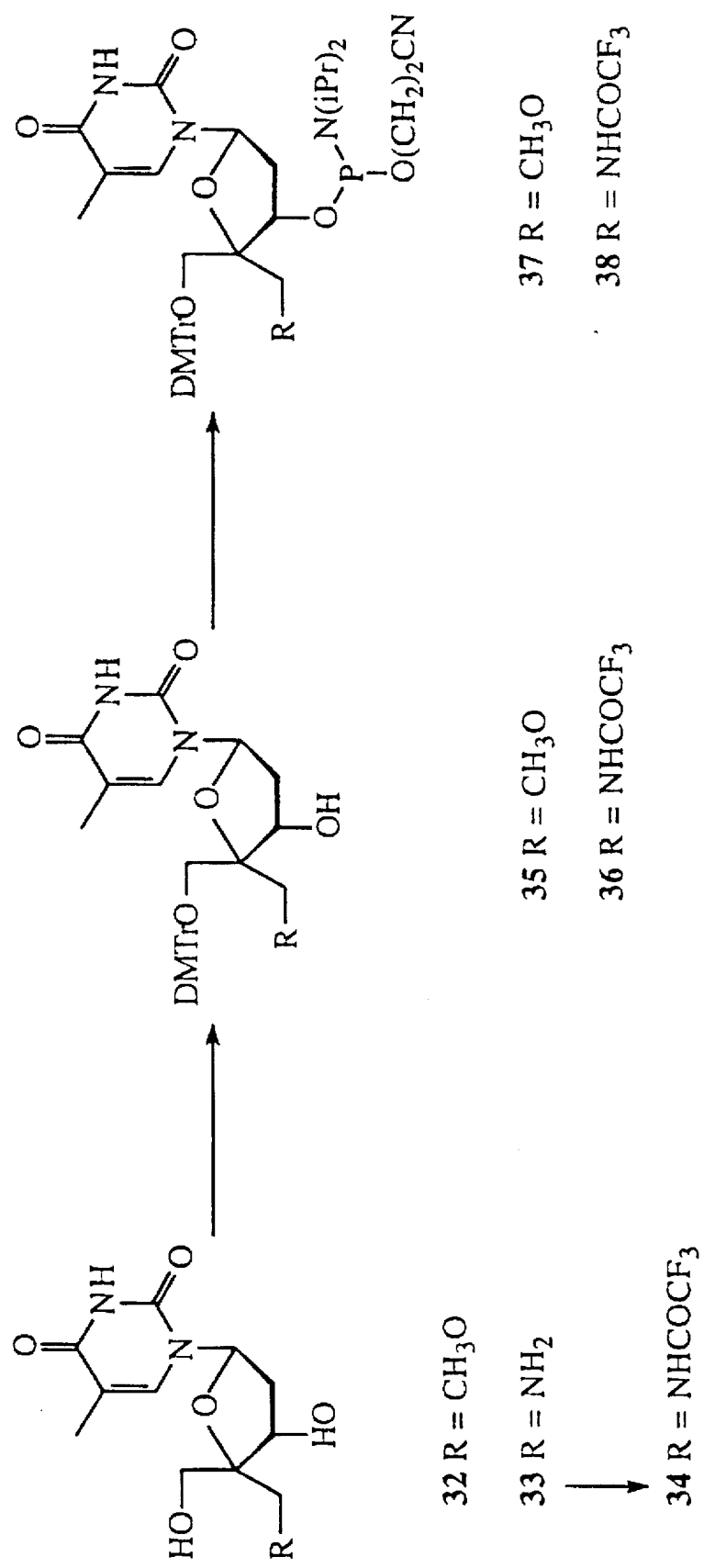
Figure 7. Reaction scheme 5.

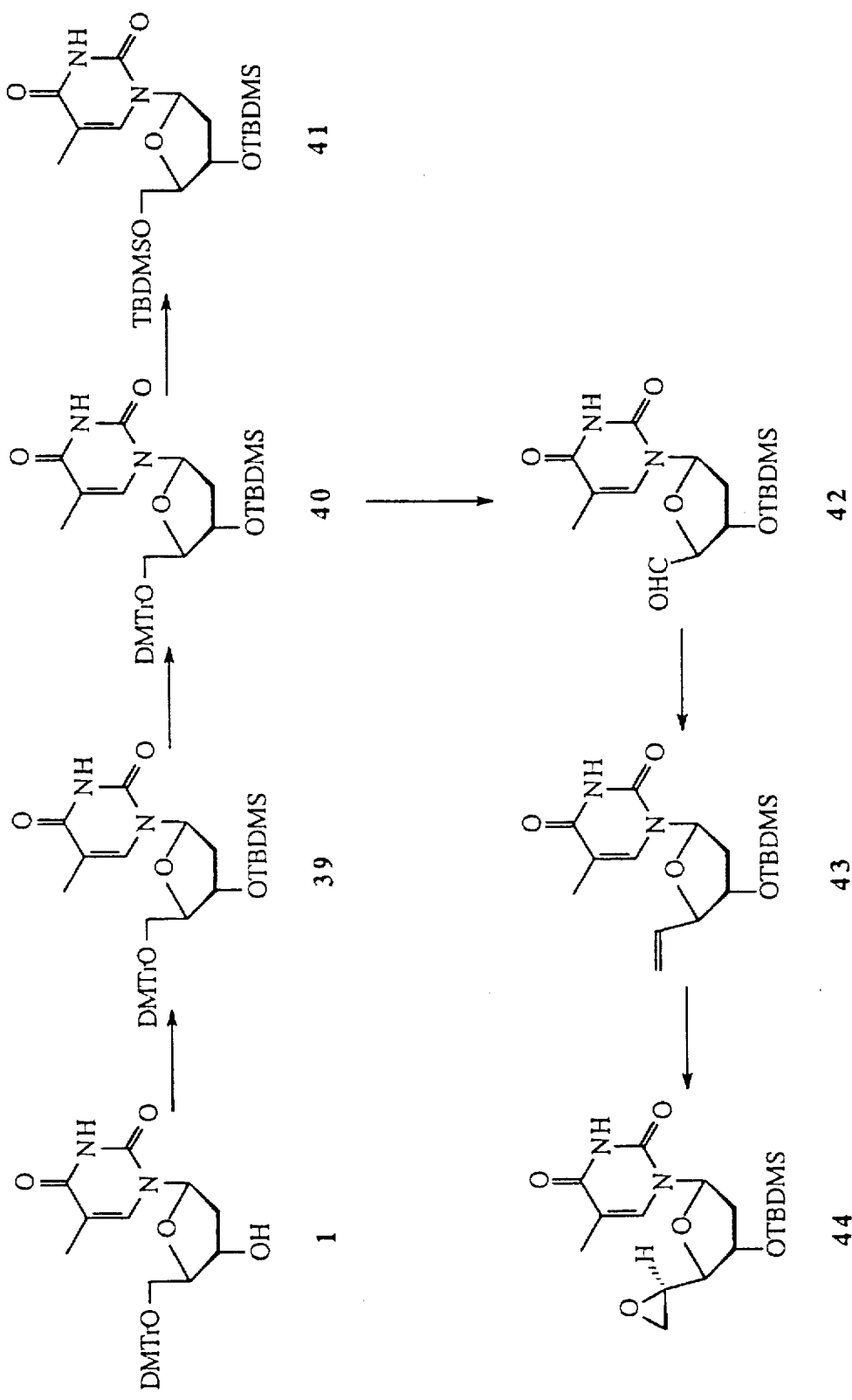
Figure 8. Reaction scheme 6.

5,681,940

SUGAR MODIFIED NUCLEOSIDES AND OLIGONUCLEOTIDES

FIELD OF THE INVENTION

The invention is in the field of polynucleotide analogs containing modified sugars.

BACKGROUND OF THE INVENTION

The therapeutic use of oligonucleotides is field of great significance and is described, for example, in, (1) Zamecnik, P. C. and Stephenson, M. L. *Proc. Natl. Acad. Sci. U.S.A.* 1978, 75, 280, 285."; (2) Uhlmann, E. and Peyman, A. *Chemical Reviews*, 1990, 90, 543–584; (3) Goodchild, J. *Bioconjugate chemistry*, 1990, 1, 165–187; and (4) Crooke, S. T. and Lebleu, B. "*Antisense Research and Applications*", CRC Press (1993)). The specific binding of antisense polynucleotides to the DNA or RNA targets of interest may inactivate the functions associated with the DNA or RNA such as replication, transcription, or translation, thereby providing a mechanism for controlling diseases such as cancer and viral infection. Therefore, the binding of an antisense oligonucleotide to a target can be used to alter gene expression, in a variety of circumstances, e.g., to interfere with viral life cycles, or the growth of cancerous cells (Stein, C. A., Cheng, Y. C. *Science*, 1993, 261, 1004–1012). In addition, some oligonucleotides also bind tightly to protein targets, thereby acting as enzyme inhibitors. Bock et al. describes oligonucleotides that inhibited human thrombin-catalyzed fibrin-clot formation in vitro (Bock, L. C., Griffin, L. C., Latham, J. A., Vermaas, E. H., Toole, J. J. *Nature*, 1992, 355, 564–566). Ecker et al describes several oligonucleotides that inhibit human herpes simplex virus at below 1.0 μmol. Polynucleotides that have enzyme inhibiting properties can readily be found by using combinatorial technology (Ecker, D. J., Vickers, T. A., Hanecak, R., Driver, V., Anderson, K. *Nucleic Acids Res.* 1993, 21, 1853–1856).

An oligonucleotide containing a 5'-C-methyl branched nucleoside has been reported to show enhanced nuclease resistance (Saha, A. K. et al., a poster in 206th ACS Meeting, Chicago, 1993). An oligonucleotide containing 2'-O-methyl nucleosides has also been reported to show improved stability to nucleases and enhanced binding affinity to RNA (a. Inoue, H., Hayase, Y., Imura, A., Iwai, S., Miura, K., Ohtsuka, E., *Nucleic Acids Res.* 1987, 15, 6131; b. Shibahara, S., Mukai, S., Morisawa, H., Nakashima, H., Cobayashi, S., Yamamoto, N. *Nucleic Acids Res.* 1989, 17, 239). An oligonucleotide containing 1'-substituted nucleoside has been reported to show some nuclease resistance (Ono, A., Dan, A., Matsuda, A. *Bioconjugate Chemistry*, 1993, 4, 499–508).

Besides having a specific binding affinity to a complementary target polynucleotide sequence, antisense oligonucleotides desirably meet the requirements for therapeutic purposes, e.g., potency, bioavailability, low toxicity, and low cost. Since oligonucleotides having the natural phosphodiester backbone are labile to nucleases and do not readily penetrate the cell membrane, researchers have attempted to make polynucleotide backbone modifications that improve nuclease resistance and cellular uptake. A major shortcoming of oligonucleotides analogs used for antisense is that the modified internucleotide linkages eliminate the RNAse H activation of antisense oligonucleotides, which degrades the RNA strand to which the oligonucleotide analog binds. Therefore, it is desirable to provide polynucleotide analogs with enhanced nuclease resistance and cellular uptake, while retaining the property of activating RNase H.

SUMMARY OF THE INVENTION

The present invention provides various novel sugar modified nucleosides and corresponding sugar modified oligonucleotides that have properties superior to natural RNA and DNA oligonucleotides when used for antisense, diagnostic, or other purposes.

The compounds of the invention include various nucleosides that have been modified so as to comprise substitutions at positions C1', C3', C4' or C5' of the sugar moiety of the nucleoside.

Another aspect of the invention is to provide oligonucleotide that comprise one or more of the sugar modified nucleosides of the invention.

Another aspect of the invention is to provide conjugates of oligonucleotide that comprise one or more of the sugar modified nucleosides of the invention.

BRIEF DESCRIPTION OF THE FIGURES

FIG. 2. The figure shows reaction scheme 1, for the synthesis of 3'-C-branched thymidine.

FIG. 3. The figure shows reaction scheme 2, for the synthesis of 3'-C-branched thymidine.

FIG. 4. The figure shows reaction scheme 3, for the synthesis of 5'-C-branched thymidine.

FIG. 5. The figure shows reaction scheme 4, for the synthesis of 4'-C-branched thymidine.

FIG. 6. The figure shows reaction scheme 5, for the synthesis of 4'-C-branched thymidine.

FIG. 7. The figure shows reaction scheme 6, for the synthesis of 1'-C-branched thymidine.

FIG. 8. The figure shows reaction scheme 7, for the synthesis of 1'-C-branched thymidine.

ABBREVIATIONS AND DEFINITIONS

Figure 1:
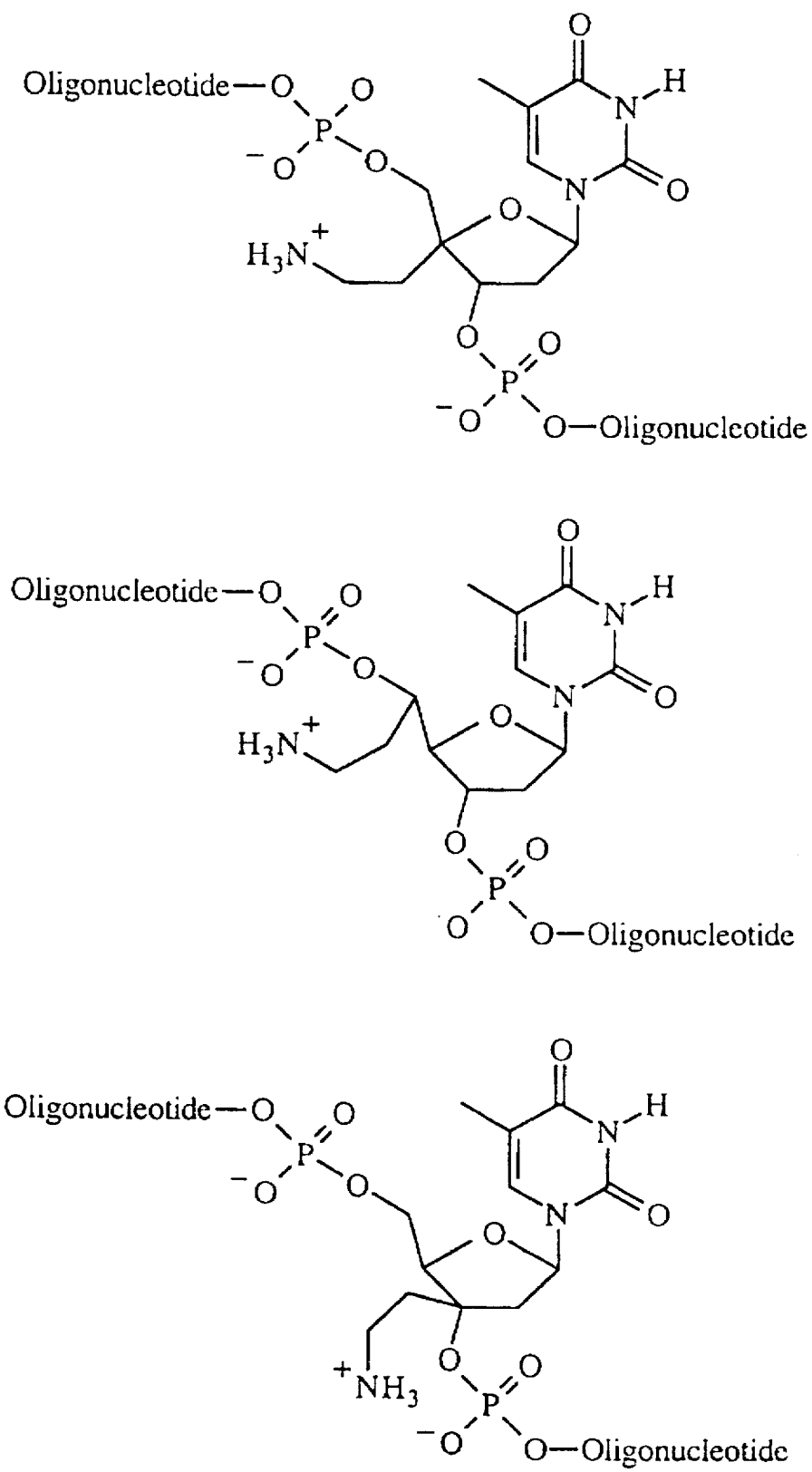
FIG. 1. The figure shows embodiments of the oligonucleotides of the invention in which the nucleoside substituents are substituted with a positively charged moiety.

DMTr=4,4'-dimethoxytrityl
CEPA=2-cyanoethyl-(N,N'-diisopropyl)phosphoramido
TBDMS=t-Butyldimethylsilyl
Ac=acetyl
TBDMSM=t-butyldimethylsiloxymethyl
$N_3$=azido
OTs=tosyl The term "nucleoside," as used herein, refers to a compound comprising a purine or pyrimidine base (or derivative thereof) covalently joined to a 5 carbon cyclic sugar (furanose), e.g. ribose, 2'-deoxyribose, and 2',3'-dideoxyribose. The term "nucleoside" is used broadly so as to include the sugar modified nucleosides of the invention.

The term "polynucleotide," as used herein, refers to polymers comprising of two or more nucleoside moieties, wherein each nucleoside moiety is joined to one (terminal) or two (internal) other nucleoside moieties through internucleoside linkages such as phosphodiester linkages, peptide linkages, phosphonate linkages, phosphorothioate linkages, and the like. RNA and DNA are examples of polynucleotides. The term "polynucleotide", as used herein, unless noted otherwise, is used broadly so as to include the sugar modified polynucleotides of the invention.

The term "oligonucleotide", as used herein, is to refer to relatively small polynucleotides, e.g. polynucleotides of between 2 and about 50 base pairs in length; however oligonucleotide may be significantly longer.

The term "hydroxyl blocking group" as used herein is readily understood by the person of ordinary skill in the art of organic chemistry, examples of hydroxyl blocking groups, and other blocking groups, can be found (among other places) in Greene and Wuts, "Protective Groups in Organic Synthesis" John Wiley & Sons, NY, N.Y. (1991).

The terms "base" and nucleoside base" as used herein refer to heterocyclic nucleotide bases found in naturally occurring nucleic acid such as adenine, cytosine, hypoxanthine, uracil, thymine, guanine and analogs thereof, including non-naturally occurring bases that are capable of forming base-pairing relationships with naturally occurring nucleotide bases. Such non-naturally occurring heterocyclic bases include, but are not limited to, aza and deaza pyrimidine analogs, aza and deaza purine analogs as well as other heterocyclic base analogs, wherein one or more of the carbon and nitrogen atoms of the purine and pyrimidine rings have been substituted by heteroatoms, e.g. oxygen, sulfur, selenium, phosphorus, and the like.

DESCRIPTION OF THE SPECIFIC EMBODIMENTS

The subject invention provides novel nucleosides and oligonucleotide having desirable properties for use in antisense, diagnostic, and other methods employing oligonucleotides. The compounds of the invention include various nucleosides that have been modified so as to comprise substitutions at position C1', C3', C4' or C5' of the sugar moiety of the nucleoside. The nucleosides of the invention may comprise one or more substitutions so as to adapt the nucleoside for solid phase synthesis or related synthetic techniques, e.g., the subject nucleosides may be in a phosphoramidite derivative with 5'-dimethoxytrityl or other protecting groups. The subject invention also provides oligonucleotides comprising one or more of the sugar modified nucleosides of the invention in a nucleic acid chain.

Adding a suitable substituent at positions C3' or C5' of a nucleoside changes the environment around the phosphodiester backbone of oligonucleotides containing these sugar modified nucleosides. Preferably, a bulky substituent at C3' or C5' is used to inhibit unwanted interactions with enzymes or their active sites. These C3' or C5' substituents are predicted to make the phosphodiester backbone of oligonucleotides inaccessible to many enzymes. As result of the presence of the substituents, oligonucleotides containing these C3' or C5' branched nucleosides may be more nuclease resistant, as compared with DNA or RNA. Substituents at the C1' and C4' positions of nucleosides may exert the same desirable effects as those at C3' and C5' position of nucleosides. In those embodiments of the invention where the subject oligonucleotides comprise positively charged aminoalkyl modified sugars, the net negative charges on the subject oligonucleotides at the physiological conditions are reduced so that the double helix formed by at least one strand of these oligonucloetides can be more stable than a corresponding unmodified oligonucleotide (see FIG. 1). Thus, in those embodiments of the invention comprising aminoalkyl modified sugars, or similar positively charged substituents, the binding affinity between the subject oligonucleotides and a polynucleotide hybridization target may be improved by the positive charge. It will be appreciated by a person of ordinary skill in the art that the above stated theories, while providing guidance in the use and design of additional embodiments of the invention, need not be correct in order to make or use the invention provided herein.

One embodiment of the invention is sugar modified nucleosides having the formula:

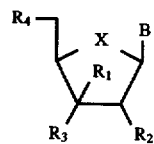
(45)

Where $R_1$ may be alkyl, aralkyl, aryl, substituted alkyl, substituted aralkyl, substituted alkyl, substituted aryl, where the substituents may be $NO_2$, CN, $N_3$, COOEt, OH, SH, $CONH_2$, CONHR, $CONR_2$, COOH, OAC, $NH_2$, NHAc, $NMe_2$, $CF_3CONH$, OR, SR, $SO_2CH_3$, $CF_3$, F, Cl, Br, I, OTs, $^+NMe_3$, CH=CHR, C=CR, where R is alkyl; $R_2$ may be H, OH, alkoxy, aryloxy; $R_3$ may be OH, O-CEPA; $R_4$ may be OH or a hydroxyl blocking group; B is a heterocyclic nucleoside base; X may be O, S, NH, $CH_2$.

The heterocyclic nucleoside base, B, of the sugar modified nucleosides of the invention, as represented in formulae 45, 46, 47, 48, 49, and 50, may be any heterocyclic nucleoside base, either naturally occurring or non-naturally occurring. Thus, heterocyclic nucleoside bases that may be base moieties in the sugar modified nucleosides of the invention may be purines (e.g., adenine, guanine, or xanthine), pyrimidines (e.g., thymine, uracil, cytosine), and heterocyclic analogs and tautomers thereof. Suitable heterocyclic bases that may serve as the base moiety of the nucleoside compounds of the invention are those bases that may be incorporated into one strand of a double-stranded polynucleotide so as to maintain a base pairing structural relationship with a naturally occurring base on the complementary strand of the polynucleotide. Additionally, the base moiety of the nucleoside compounds of the invention are joined to the sugar moiety at a site on the base that permits the base to enter into base pairing relationships, as previously discussed.

Another embodiment of the invention is to provide nucleotides having the formula:

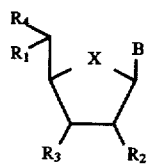
(46)

Where $R_1$ may be alkyl, aralkyl, aryl, substituted alkyl, substituted aralkyl, substituted alkyl, substituted aryl, where the substituents may be $NO_2$, CN, $N_3$, COOEt, OH, SH, $CONH_2$, CONHR, $CONR_2$, COOH, OAC, $NH_2$, NHAc, $NMe_2$, $CF_3CONH$, OR, SR, $SO_2Me$, $CF_3$, F, Cl, Br, I, OTs, $^+NMe_3$, CH=CHR, C=CR, where R is alkyl; $R_2$ may be H, OH, alkoxy, aryloxy; $R_3$ may be OH, O-TBDMS, O-CEPA; $R_4$ may be OH, CHO, or a hydroxyl blocking group; B is a heterocyclic nucleoside base; X may be O, S, NH, $CH_2$. Another embodiment of the invention is nucleosides having the formula:

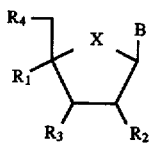
(47)

Where $R_1$ may be alkyl, aralkyl, aryl, substituted alkyl, substituted aralkyl, substituted alkyl, substituted aryl, where the substituents may be $NO_2$, CN, $N_3$, COOEt, OH, SH, $CONH_2$, CONHR, $CONR_2$, COOH, OAC, $NH_2$, NHAc, $NMe_2$, $CF_3CONH$, OR, SR, $SO_2Me$, $CF_3$, F, Cl, Br, I, OTs, $^+NMe_3$, CH=CHR, C=CR, where R is alkyl; $R_2$ may be H, OH, alkoxy, aryloxy; $R_3$ may be OH, OTBDMS, O-CEPA; $R_4$ may be OH or a hydroxyl blocking group; B is a heterocyclic nucleoside base; X may be O, S, NH, $CH_2$.

Another aspect of the invention is to provide nucleotides having the formula:

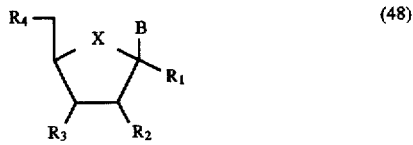

(48)

Where $R_1$ may be alkyl, aralkyl, aryl, substituted alkyl, substituted aralkyl, substituted alkyl, substituted aryl, where the substituents may be $NO_2$, CN, $N_3$, COOEt, OH, SH, $CONH_2$, CONHR, $CONR_2$, COOH, OAC, $NH_2$, NHAc, $NMe_2$, $CF_3CONH$, OR, SR, $SO_2Me$, $CF_3$, F, Cl, Br, I, OTs, $^+NMe_3$, CH=CHR, C≡CR, where R is alkyl; $R_2$ may be H, OH, alkoxy, aryloxy; $R_3$ may be OH, O-MBn, O-CEPA; $R_4$ may be OH, or a hydroxyl blocking group; B is a heterocyclic nucleoside base; X may be O, S, NH, $CH_2$.

Another aspect of the invention is to provide various epoxide derivatives of the sugar modified nucleosides of the invention having the formulae:

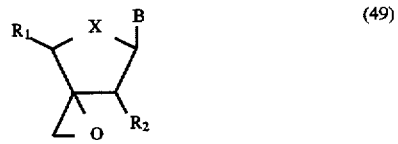

(49)

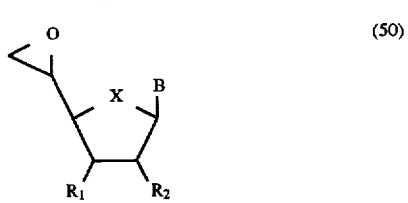

(50)

where R is selected from the group consisting of $CH_2OH$, $CH_2ODMTr$, CHO, COOH, and COOEt; and X is selected from the group consisting of O, S, NH, and $CH_2$. The epoxides may be in either of the two possible stereochemical orientations.

The sugar modified nucleoside of the invention may be synthesized by reference to the examples provided in the examples section of this application. A person of ordinary skill in the art of organic chemistry may, given the example provided herein, synthesize numerous compounds of the invention for which explicit syntheses are not given.

Oligonucleotides containing sugar modified nucleosides

The polynucleotides of the invention comprise one or more of the sugar modified nucleosides of the invention, wherein a sugar modified nucleoside of the invention is joined to either a second sugar modified nucleoside or an unmodified nucleoside, wherein the nucleosides are joined through an internucleoside linkage. The sugar modified nucleosides for incorporation into the oligonucleotides of the invention include the compounds of formulae 45, 46, 47, and 48. The polynucleotide analogs of the invention are not limited with respect to the number of possible nucleoside subunits in an individual polynucleotide analog; however, it is generally more convenient to synthesize short polynucleotide analogs, e.g., polynucleotides analogs comprising less than 50 bases.

The individual nucleosides of the invention may be joined to one another through internucleoside linkages so as to produce novel oligonucleotide having desired nucleoside base sequences. The internucleoside linkages may be C3' to C5' linkage or a C2' to C5' linkage. The term "internucleoside linkage" as used herein refers not only to the phosphodiester backbone of the type that forms internucleoside linkages in DNA (dideoxyribonucleic acid) and RNA (ribonucleic acid), but also to a variety of other moieties that serve the same structural function as phosphodiester linkages in DNA and RNA. Examples of other internucleoside linkages suitable for the oligonucleotides of the invention include phosphorothioates, methylphosphonates, phosphorodithioates, boron phosphonates, selenophosphonates, phosphoramidates, acetamidates, and the like. Descriptions of the synthesis and use of various internucleoside linkages can be found, among other places in U.S. Pat. No. 5,256,775, PCT Publication WO93/24507, PCT Publication WO92/05186, U.S. Pat. No. 5,264,562, PCT Publication WO92/02534, PCT Publication WO94/06811, PCT Publication WO93/17717, U.S. Pat. No. 5,212,295, U.S. Pat. No. 5,292,875, U.S. Pat. No. 5,218,103, U.S. Pat. No. 5,166,387, U.S. Pat. No. 5,151,516, U.S. Pat. No. 4,814,448, U.S. Pat. No. 4,814,451, U.S. Pat. No. 4,096,210, U.S. Pat. No. 4,094,873, U.S. Pat. No. 4,092,312, U.S. Pat. No. 4,016,225, U.S. Pat. No. 4,007,197, and the like.

Polynucleotides of the invention having a desired base sequence may readily be produced using nucleic acid polymer synthesis techniques that are well known to the person of ordinary skill in the art of organic chemistry. The polynucleotides of the invention are preferably synthesized using phosphoramidite chemistry to incorporate one or more of the novel nucleoside of the invention into a polynucleotide analog. Branched substituents at C3' or C5' of the nucleosides of the invention may reduce the coupling rate, depending on the size of the substituents. Therefore, for some bulky substituent branched nucleosides, coupling time may need to be extended to up to 10 times or more. The repeated couplings with fresh reagents and use of more concentrated coupling reagents may also be used to increase the rate of the coupling reaction, when necessary. After synthesis oligonucleotides may be worked up in the same way as standard unmodified oligonucleotide, that is, cleaving from solid supports by using 30% ammonia, deprotection under 55° C. for 8 h, and purified by reverse phase HPLC.

In order to verify both the purity of oligonucleotides and incorporation of desired sugar modified nucleosides, the purified oligonucleotides may be characterized by analysis of enzyme digestion products using enzymes such as snake venom phosphodiesterase and bacterial alkaline phosphatase to degrade the oligonucleotides. The degraded products may then be subjected to HPLC analysis (or other separation techniques) and comparison with the authentic nucleoside samples. The structure of purified oligonucleotides can also be verified by mass spectroscopy such as electrospray technique.

Another aspect of the invention is conjugates of the sugar modified oligonucleotides of the invention. Amino-, hydroxy, thio-, or carboxylalkyl linkers may be attached to the C1', C3', C4', and C5' position of the subject nucleosides so as to provide a site for conjugating a moiety of interest to the oligonucleotide. Linkers attached to positions C1' and C3' may be used to direct the conjugating moiety to the minor grooves of a double stranded nucleic acid, while linkers attached to position C4' may be used to direct the conjugating moiety to the major grooves. Linkers attached to position C5' may be used to direct a conjugate moiety to either the major or minor grooves of a double stranded nucleic acid, depending on the stereochemistry of the linker at C5'. Through linkers, a wide variety of functional moieties such as artificial nuclease, crosslinking reagents, intercalators, and reporter molecules can be linked to and located in the desired position.

Utility and Administration:

As the oligonucleotides of the invention are capable of significant single-stranded or double-stranded target nucleic acid binding activity to form duplexes, triplexes or other forms of stable association, with naturally occurring polynucleotides and structural analogs thereof, the oligonucleotides of the invention may be used in most procedures that employ conventional oligonucleotides. Thus, the oligonucleotides of the invention may be used as, for example, polynucleotide hybridization probes, primers for the polymerase chain reaction (and similar cyclic amplification reactions, sequencing primers, and the like. The oligonucleotides of the invention may also be used in the diagnosis and therapy of diseases. Therapeutic applications of the oligonucleotides of the invention include the specific inhibition of the expression of genes (or the inhibition of translation of RNA sequences encoded by those genes) that are associated with either the establishment or the maintenance of a pathological condition through the use of antisense oligonucleotides. The oligonucleotides of the invention may be used to mediate antisense inhibition of numerous genetic targets. Exemplary genes or RNAs encoded by those genes that may be targeted through antisense oligonucleotides of the invention include oligonucleotides that encode enzymes, hormones, serum proteins, transmembrane proteins, adhesion molecules (LFA-1, GPII$_b$/III$_a$, ELAM-1, VACM-1, ICAM-1, E-selection, and the like), receptor molecules including cytokine receptors, cytokines (IL-1, IL-2, IL-3, IL-4, IL-6 and the like), oncogenes, growth factors, and interleukins. Target genes or RNAs may be associated with any pathological condition such as those associated with inflammatory conditions, cardiovascular disorders, immune reactions, cancer, viral infections, bacterial infections, yeast infections, parasite infections and the like.

Oligonucleotides of the present invention are suitable for use in both in vivo and ex vivo therapeutic applications. Indications for ex vivo uses include treatment of cells such as bone marrow or peripheral blood in conditions such as leukemia (chronic myelogenous leukemia, acute lymphocytic leukemia) or viral infection. Target genes or RNAs encoded by those genes that may serve as targets for cancer treatments include oncogens, such as ras, k-ras, bcl-2, c-myb, bcr, c-myc, c-abl or overexpressed sequences such as mdm2, oncostatin M, IL-6 (Kaposi's sarcoma), HER-2 and translocations such as bcr-abl. Viral gene sequences or RNAs encoded by those genes such as polymerase or reverse transcriptase genes of herpesviruses such as CMV, HSV-1, HSV-2, retroviruses such as HTLV-1, HIV-1, HIV-2, or other DNA or RNA viruses such as HBV, HPV, VZV, influenza virus, adenoviruses, flaviviruses, rhinovirus and the like are also suitable targets. Application of specifically binding oligonucleotides may be used in conjunction with other therapeutic treatments. Other therapeutic uses for oligonucleotides of the invention include (1) modulation of inflammatory responses by modulating expression of genes such as IL-1 receptor, IL-1, ICAM-1 or E-Selection that play a role in mediating inflammation and (2) modulation of cellular proliferation in conditions such as arterial occlusion (restenosis) after angioplasty by modulating the expression of (a) growth or mitogenic factors such as non-muscle myosin, myc, fox, PCNA, PDGF or FGF or their receptors, or (b) cell proliferation factors such as c-myb. Other suitable proliferation factors or signal transduction factors such as TGFa, IL-6, gINF, protein kinase C, tyrosine kinases (such as p210, p190), may be targeted for treatment of psoriasis or other conditions. In addition, EGF receptor, TGFa or MHC alleles may be targeted in autoimmune diseases.

The oligonucleotides of the invention may also be advantageously substituted for conventional oligonucleotides in many non-therapeutic techniques such as hybridization to detect nucleic acid sequences, the polymerase chain reaction, and the like. These non-therapeutic techniques are well known to the person of ordinary skill in the art of molecular biology and can be found, for example, in Sambrook et al. *Molecular Cloning Techniques 2nd Edition* Clod Spring Harbor (1989).

Delivery of oligonucleotides of the invention into cells may be enhanced by any suitable method including calcium phosphate, DMSO, glycerol or dextran transfection, electroporation or by the use of cationic anionic and/or neutral lipid compositions or liposomes by methods described (International Publications Nos. WO 90/14074, WO 91/16024, WO 91/17424, U.S. Pat. No. 4,897,355). The oligonucleotides may be introduced into cells by complexion with cationic lipids such as DOTMA (which may or may not form liposomes) which complex is then contacted with the cells. Suitable cationic lipids include but are not limited to N-(2,3-di(9-(Z)-octadecenyloxyl))-prop-1-yl-N,N,N-trimethylammonium (DOTMA) and its salts, 1-O-oleyl-2-O-oleyl-3-dimethylaminopropyl-β-hydroxyethylammonium and its salts and 2,2-bis(oleyloxy)-3-(trimethylammonio) propane and its salts.

Enhanced delivery of the invention oligonucleotides may also be mediated by the use of (i) viruses such as Sendai virus (Bartzatt, R., *Biotechnol Appl Biochem.*, 1989, 11, 133–135) or adenovirus (Wagner, E. et al, *Proc Natl Acad Sci. USA*, 1992, 89, 6099–6013); (ii) polyamine or polycation conjugates using compounds such as polylysine, protamine or Na, N$_{12}$-bis (ethyl)spermine (Wagner, E. et al, *Proc Natl Acad Sci. USA*, 1991, 88, 4255–4259; Zenke, M. et al, *Proc. Natl. Acad. Sci. USA*, 1990, 87, 3655–3659; Chank, B. K. et al, *Biochem Biophys Res Commun.*, 1988, 157, 264–270; U.S. Pat. No. 5,138,045); (iii) lipopolyamine complexes using compounds such as lipospermine (Behr, J.-P. et al, *Proc Natl Acad Sci. USA*, 1989, 86, 6982–6986; Loeffler, J. P. et al, *J. Neurochem.*, 1990, 54, 1812–1815); (iv) anionic, neutral or pH sensitive lipids using compounds including anionic phospholipids such as phosphatidyl glycerol, cardiolipin, phosphatidic acid or phosphatidylethanolamine (Lee, K.-D. et al, *Biochem Biophys ACTA*, 1992, 1103, 185–197; Cheddar, G. et al, *Arch Biochem Biophys*, 1992, 294, 188–192; Yoshimura, T., et al, *Biochem Int.*, 1990, 20, 697–706); (v) conjugates with compounds such as transferrin or biotin or (vi) conjugates with proteins (including albumin or antibodies), glycoproteins or polymers (including polyethylene glycol) that enhance pharmacokinetic properties of oligonucleotides in a subject. As used herein, transfection refers to any method that is suitable for delivery of oligonucleotides into cells. Any reagent such as a lipid or any agent such as a virus that may be used in transfection protocols is collectively referred to herein as a "permeation enhancing agent". Delivery of the oligonucleotides into cells may be via cotransfection with other nucleic acids such as (i) expressable DNA fragments encoding a protein(s) or a protein fragment or (ii) translatable RNAs that encode a protein(s) or a protein fragment.

The oligonucleotides of the invention may thus be incorporated into any suitable formulation that enhances delivery of the oligonucleotides into cells. Suitable pharmaceutical formulations also include those commonly used in applications where compounds are delivered into cells or tissues by topical administration. Compounds such as polyethylene glycol, propylene glycol, azone, nonoxonyl-9, oleic acid, DMSO, polyamines or lipopolyamines may be used in topical preparations that contain the oligonucleotides.

Synthesis of 3'-C-Substituent branched nucleosides

Hydroxyl group substitution at C3' of nucleosides by other functional groups with preservation of hydrogen at C3' position has been described in, among other places, De Clercq, E., *Antiviral Res.* 1989, 12, 1–20. Hydrogen substitution at C3' of nucleosides by other functional groups has been reported in Fedorov, I. I., Kazmina, E. M., Novicov, N. A., Gurskaya, G. V., Bochkarev, A. V., Jasko, M. V., Victorova, L. S., Kuhkanova, M. K., Balzarini, J., De Clercq, E. *J Med Chem.* 1992, 35, 4567–4575. The invention provides several procedures for the preparation of a large number of different 3'-C-branched nucleosides. Examples of methods for preparing 3'-C-branched thymidines are shown in REACTION SCHEME 1 and 2 (FIGS. 2 and 3, respectively). These procedures may be readily adapted for the synthesis of other nucleosides of the invention, including embodiments of the invention in which the nucleosides comprise a base other than thymine. Compound 1 is prepared by reaction of thymidine with 4,4'-dimethoxytrityl chloride in pyridine. Oxidation of Compound 1 with $CF_3COOH$/Pyridine/DCC/DMSO affords a ketone, Compound 2, which is converted to olefinic Compound 3 by treatment with an ylide prepared from sodium hydrogen and methyltriphenylphosphonium bromide. Treatment of Compound 3 with m-chloroperbenzoic acid affords an epoxide, Compound 4, which has the stereochemistry as shown in REACTION SCHEME 1 (FIG. 2) as expected from the reaction mechanism and may be verified by using NMR or other analytical techniques. Treatment of Compound 4 with a wide variety of nucleophilic reagents affords 3'-C-substituent branched thymidine derivatives in which 3'-C-hydroxyl group remains in the same orientation as in thymidine. The nucleophiles are expected to attack from the less hindered carbon of the epoxide ring. Treatment with lithium aluminum hydride affords 3'-C-methyl branched thymidine. Treatment with sodium cyanide affords 3'-C-cyanomethyl branched thymidine. Treatment with sodium nitrite affords 3'-C-nitromethyl branched thymidine. Treatment with nitromethane affords 3'-nitroethyl branched thymidine. Reduction of 3'-C-nitromethyl and 3'-C-nitroethyl branched thymidines with sodium borohydride and palladium on charcoal affords 3'-C-aminomethyl and 3'-C-aminoethyl branched thymidines, which are treated with ethyl thiotrifluoroacetate to give 3'-trifluoroacetamidomethyl and 3'-C-trifluoroacetamidoethyl branched thymidine. 3'-C-Aminomethyl branched thymidine can also be prepared by treatment of Compound 4 with ammonia. Treatment of Compound 4 with sodium hydroxide affords 3'-hydroxymethyl branched thymidine, which is protected with acetyl group to afford 3'-C-acetocymethyl branched thymidine. Treatment of Compound 4 with sodium methoxide affords 3'-C-methoxymethyl branched thymidine. Treatment of Compound 4 with sodium azide affords 3'-C-azidomethyl branched thymidine. Treatment of Compound 4 with sodium hydrogen sulfide affords 3'-C-thiolmethyl branched thymidine, which is protected by acetyl to give 3'-C-acetylthiomethyl branched thymidine. All these products or their protected derivatives are converted to the corresponding phosphoramidites, Compound 6 (REACTION SCHEME 1), by the standard procedure (F. Eckstein, "*Oligonucleotide synthesis*", Oxford University Press (1991)).

For some reactions involving organometalic reagents, the amide group of thymine needs protection; t-butylmethoxysiloxymethyl (TBDMSM) is preferred for use as the protecting group. Compound 4 is treated with p-methoxybenzyl bromide to give the methoxybenzyl protected epoxide, Compound 7. Treatment of Compound 7 with lithium organocuprate reagents affords a variety of 3'-C-alkyl or 3'-C-aryl branched thymidines. Treatment of Compound 7 with ethoxycarbonylalkyl zinc reagents affords ethoxycarbonylalkyl branched thymidines, which can be readily converted to other functionalities. Some cyano-substituted alkyl cadmium reagents are used to convert Compound 7 to a cyanoalkyl branched thymidines. Treatment of Compound 7 with substituted alkyl alcohol and sodium hydride affords substituted alkoxymethyl branched thymidines. The substituents of substituted alkyl alcohols include, but are not limited to, $NO_2$, CN, and COOEt. Reduction of 3'-C-nitroalkyl branched thymidine with sodium borohydride and Pd/C affords the corresponding 3'-C-aminoalkyl branched thymidines, which are protected with trifluoroacetyl group. Deprotection of TBDMSM group is achieved by using tetrabutylammonium fluoride. Treatment of 3'-C-branched thymidines or their protected derivatives with β-cyanoethyl-N,N-diisopropylchlorophosphoramidite affords the corresponding phosphoramidites, compound 10. For the above described reactions, the products resulting from attack on less hindered carbon of the epoxide are expected to predominate. Confirmation of the stereochemistry of the 3'-C-branched nucleosides can be accomplished by using NMR spectroscopy or other analytical techniques.

Synthesis of 5'-C-Substituent branched nucleosides

This invention provides a large number of 5'-C-substituent branched nucleosides. An example of a method of preparing 5'-C-branched thymidines is shown in REACTION SCHEME 3 (FIG. 4). This procedure may be readily adapted for the synthesis of other nucleosides of the invention, including embodiments of the invention in which the nucleosides comprise a base other than thymine. For some reactions, there is no need to protect amide proton of thymidine, but for most of the reactions in REACTION SCHEME 3 (FIG. 4) it is necessary to protect the amide proton. As in the case of Compound 7 in REACTION SCHEME 2 (FIG. 3), Compound 11 may be protected with a TBDMSM group. Compound 11 is prepared by reaction of thymidine with 4,4'-dimethoxytrityl chloride, followed by successive treatment with t-butyldimethychlorosilane and 80% acetic acid (Counde O-Yang et al, *Tetrahedron Lett.* 1992, 33, 37–40). Oxidation of Compound 11 with $CF_3COOH$/Pyridine/DCC/DMSO affords the aldehyde, Compound 12. Treatment of Compound 12 with any of a variety of nucleophiles affords Compound 13, which contain two diastereomers from each reaction. The two diastereomers resulting from each reaction are separated by chromatography and their stereochemistry of some diastereomers is assigned by using X ray crystallography. In some cases two diastereomers are used for further reactions without separation. Treatment of Compound 12 with sodium cyanide affords 5'-C-cyano branched thymidine. Treatment with sodium azide affords 5'-C-azido branched thymidine. Treatment with potassium nitrite affords 5'-C-nitro branched thymidine. Treatment with nitromethane in the presence of triethylamine affords 5'-C-nitromethyl branched thymidine. Treatment of Compound 12 with lithium organocuprate reagents or organozinc reagents affords a variety of 5'-C-alkyl, aryl, substituted alkyl, or substituted aryl branched thymidines. The substituents in substituted alkyl, and substituted aryl can be $NO_2$, CN, COOEt. Reduction of 5'-C-nitroalkyl or 5'-C-nitroaryl branched thymidines with sodium borohydride affords 5'-C-aminoalkyl or 5-C-'aminoaryl branched thymidines, which are protected with trifluoroacetyl group. Compound 13 reacts with dimethoxytrityl chloride to give 5'-C-dimethoxytrityl-5'-C-substitutent branched thymidines (compound 14). Treatment of compound 14 with tetrabutylammonium fluoride and cerium ammonium nitrate for removal of t-butyldimethylsilyl and t-butyldimethylsiloxymethyl groups affords compound 15, which is converted to the corresponding phosphoramidite compound 16.

Synthesis of 4'-Substituted nucleosides

A number of 4'-Substituted nucleosides have been reported in O-Yang C., Wu, H. Y., Fraser-Smith, E. B., Walker, K. A. M. *Tetrahedron Lett.*, 1992, 33, 37–40. The invention provides a number of novel 4'-substituted nucleosides. Examples of methods for preparing 4'-substituted thymidines are provided in REACTION SCHEMES 4 and 5 (FIGS. 5 and 6, respectively). These procedures may be readily adapted for the synthesis of other nucleosides of the invention, including embodiments of the invention in which the nucleosides comprise a base other than thymine. Compound 17, an aldehyde derivative, is prepared from Compound 11 according to a known reaction procedure (a. O-Yang C., Wu, H. Y., Fraser-Smith, E. B., Walker, K. A. M. *Tetrahedron Lett.*, 1992, 33, 37–40; b. Jones, G. H., Taniguchi, M., Tegg, D., Moffatt, J. G. *J. Org. Chem.* 1979, 44, 1309–17). Compound 17 is heated with carbon tetrabromide in chloroform in the presence of triphenylphosphine to give the bromide, Compound 18. Reduction of Compound 18 with sodium borohydride affords the alcohol, Compound 19, which is protected by dimethoxytrityl to give Compound 20. Treatment of Compound 20 with a variety of nucleophilic reagents affords 4'-substituent thymidines, Compound 21. Treatment with sodium cyanide affords 4'-cyanomethyl thymidine. Treatment with sodium nitrite affords 4'-nitromethyl thymidine. Treatment with sodium azide affords 4'-azidomethyl thymidine. Treatment with nitromethane in the presence of base affords 4'-nitroethyl thymidine. Treatment with sodium hydrogen sulfide affords 4'-thiomethyl thymidine. Treatment with sodium alkyl sulfides affords 4'-alkylthio thymidine. Treatment with sodium alkoxide affords 4'-alkoxymethyl thymidine. Treatment with lithium organocuprate reagents affords a variety of 4'-alkyl or 4'-aryl thymidines. Organozinc or organocadmium reagents are used to prepare some substituted alkyl or aryl thymidines. The substituents may be CN, COOEt. Substituted alkyl alcohols and phenols are used to prepare 4'-alkoxy- or phenoxymethyl thymidines. The substituents may be NO$_2$, CN, COOEt, OAc, which can be used for conjugate chemistry. 4'-Nitroalkyl or 4'-nitroarylthymidines are reduced with sodium borohydride to 4'-aminoalkyl or 4'-aminoaryl thymidines. Treatment of Compound 21 with tetrabutylammonium fluoride and removes t-butyldimethylsilyl and t-butyldimethylsiloxymethyl to give Compound 22, which are converted to the corresponding phosphoramidites.

Compound 12 reacts with bromonitromethane, bromoacetonitrile, and ethyl bromoacetate, respectively, to give the corresponding products 24a–c, which can be reduced to the corresponding alcohols, Compounds 25a–c. Treatment of Compound 25 with dimethoxytrityl chloride affords Compound 26. These products can be reduced to 4'-aminomethyl, formyl methyl, and hydroxymethyl thymidines, which are readily further derivatised. Treatment of Compound 26 and derivatized products thereof with tetrabutylammonium fluoride affords Compound 27, which is converted to, or properly protected and then converted to the corresponding phosphoramidites.

Synthesis of 1'-Substituted Nucleosides

1'-substituted nucleosides have been reported in Uteza, V., Chen, G-R., Tuoi, J. L. Q., Descotes, G., Fenet, B., Grouiller, A. *Tetrahedron*, 1993, 49, 8579–8588; Azhayev, A., and Gouzaev, A., Hovinen, J., Azhayeva, E., Lonnberg, H. *Tetrahedron Lett.* 1993, 34, 6435–6438). The invention provides a large number of novel 1'-substituted nucleosides. Preparation of 1'- substituted thymidine is shown in REACTION SCHEMES 6 and 7 (FIGS. 7 and 8, respectively). Compound 29 may be prepared according to a known procedure (Uteza, V., Chen, G-R., Tuoi, J. L. Q., Descotes, G., Fenet, B., Grouiller, A. *Tetrahedron*, 1993, 49, 8579–8588). 5'-Hydroxyl group of Compound 29 is protected by dimethoxytrityl to give Compound 30, which is treated with t-butyldimethylchlorosilane affords Compound 31. Treatment of Compound 31 with t-butyldimethoxysiloxymethyl chloride affords Compound 32. Treatment of Compound 32 with lithium triethoxyaluminum hydride in ether affords an aldehyde, Compound 33. Reduction of the aldehyde 33 with sodium borohydride affords Compound 34, which is converted to a bromide, Compound 34, by treatment with carbon tetrabromide and triphenylphosphine in chloroform. Treatment of Compound 34 with any of a wide variety of nucleophiles affords a number of 1'-substituted thymidines, Compound 35. Treatment with sodium cyanide, nitrite, azide affords the corresponding 1'-cyanomethyl, 1'-nitromethyl, and 1'-azidomethyl thymidines. Treatment with nitromethane affords 1'-nitroethyl thymidine. Treatment with sodium alkyl sulfides affords 1'-alkylthio branched thymidine. Treatment with sodium alkoxide affords 1'-alkoxymethyl branched thymidine. Treatment with lithium organocuprate reagents affords 1'-alkyl, or 1'-aryl, thymidines. Substituted alkyl or aryl zinc or cadmium reagents are used to prepare 1'-substituted alkyl or 1'-substituted aryl thymidines. The substituents may be COOEt, CN. Substituted alkyl alcohols and phenols are used to prepare 1'-alkoxymethyl- or 1'-phenoxymethyl thymidines. The substituents may be NO$_2$, CN, COOEt, OAc. 1'-Nitroalkyl or nitroaryl derivatives are converted to the corresponding aminoalkyl or aminoaryl derivatives, which are protected by trifluoroacetyl group. Compound 35 is treated with tetrabutylammonium fluoride to give deprotected Compound 36, which are converted to the corresponding phosphoramidites, Compound 37.

Compound 29 is fully protected with a t-butyldimethylsiloxymethyl group to give Compound 38. Hydrolysis of 1'-cyanothymidine, Compound 38 in the presence of hydrogen peroxide and base affords Compound 39. Compound 39 is treated under Hofmann rearrangement conditions to afford an amine, which subsequently treated with methyl bromide to give quarternary ammonium derivative, Compound 40. A variety of nucleophiles can be used to replace trimethylamine. Treatment of Compound 40 with sodium alkoxide affords 1'-alkoxy thymidines. Treatment with sodium alkyl sulfide affords 1'-alkylthiothymidines. Compound 40 is subjected to heat so as to produce 1'-bromothymidine, which is then treated with sodium azide, sodium nitrite, or nitromethane to give the corresponding 1'-substituted thymidines. Compound 41 is treated with tetrabutyl-ammonium fluoride and then subjected to hydrogenolysis to give deprotected Compound 42. 5'-Hydroxyl is protected with dimethoxytrityl and the resulting products, Compounds 43, are converted to the corresponding phosphoramidites, i.e., Compound 44.

EXAMPLES

The invention having been described above, may be better understood by reference to the following examples. The following examples are intended to illustrate but not to limit the invention:

Example 1.

Preparation of 5'-(4,4'-dimethoxytrityl)-3'-ketothymidine.

This compound is prepared according to a standard oxidation procedure (Tipson, "*Synthetic Procedures in Nucleic Acid Chemistry*", Vol I, P395, 1968). Commercially available 5'-(4,4'-dimethoxytrityl)thymidine, dicyclohexylcarbodiimide (3.0 equivalents), anhydrous pyridine (1.0 equivalent) are dissolved in anhydrous DMSO. A solution of trifluoroacetic acid (0.5 equivalent) in DMSO is added dropwise at 0° C. The resulting reaction mixture is stirred at room temperature overnight and water (10 equivalents) added. The mixture is stirred at room temperature for 1 h. The precipitates are filtered and washed with DMSO. The filtrate is diluted with dichloromethane, washed with brine. The crude product is purified by chromatography on silica.

Example 2.

Preparation of 5'-(4,4'-dimethoxytrityl)-3'-deoxy-3'-methylidene-thymidine.

5'-(4,4'-Dimethoxytrityl)-3'-ketothymidine dissolved in DMSO is added to a stirred, cold solution containing a phosphorus ylide prepared from triphenylmethylphosphonium bromide (1.0 equivalent) and sodium hydride (1.0 equivalent) in DMSO. The resulting reaction mixture is stirred at 40° C. for 2 h., diluted with dichloromethane, and washed with brine. The crude product is purified by chromatography on silica.

Example 3.

Preparation of 5'-(4,4'-dimethoxytrityl)-3',3'-oxomethylenethymidine.

5'-(4,4'-Dimethoxytrityl)-3'-deoxy-3'-methylidenethymidine (1.0 equivalent) dissolved in chloroform is added to a, cold, stirred solution of m-chloroperbenzoic acid (1.2 mmol) in chloroform. The resulting mixture is stirred at room temperature overnight, washed with 10% sodium bicarbonate and then brine. The crude product is purified by chromatography.

Example 4.

Preparation of 5'-(4,4'-dimethoxytrityl)-3'-methyl branched thymidine.

5'-(4,4'-Dimethoxytrityl)-3',3'-oxomethylenethymidine (1.0 mmol) dissolved in anhydrous THF is added to a stirred suspension of lithium aluminum hydride (1.0 mmol) in THF at −10° C. The resulting reaction mixture is stirred at 0° C. under nitrogen for 2 h, quenched by adding 2N sodium hydroxide aqueous solution under cooling, extracted with dichloromethane. The crude product is purified by chromatography.

Example 5.

Preparation of 3'-cyanomethyl branched 5'-(4,4'-dimethoxytrityl)thymidine.

5'-(4,4'-Dimethoxytrityl)-3',3'-oxomethylenethymidine dissolved in anhydrous DMSO is added to a stirred mixture containing sodium cyanide (1.2 equivalents) and DMSO. The reaction mixture is stirred at 50° C. overnight, diluted with chloroform, washed with brine. The crude product is purified by chromatography.

Example 6.

Preparation of 5'-(4,4'-dimethoxytrityl)-3'-nitromethyl branched thymidine.

5'-(4,4'-Dimethoxytrityl)-3',3'-oxomethylenethymidine in anhydrous DMSO is added to a stirred mixture containing sodium nitrite (2.0 equivalents) and DMSO. The reaction mixture is stirred at room temperature overnight, diluted with chloroform, washed with brine. The crude product is purified by chromatography.

Example 7.

Preparation of 3'-azidomethyl branched 5'-(4,4'-dimethoxytrityl)thymidine.

5'-(4,4'-Dimethoxytrityl)-3',3'-oxomethylenethymidine is added to a stirred aqueous solution of sodium azide (3.0 equivalents) and hexadecyltributylphosphonium bromide (0.1 equivalent). The resulting reaction mixture is stirred at 50° C. overnight, extracted with chloroform. The crude product is purified by chromatography on silica.

Example 8.

Preparation of 3'-aminomethyl branched 5'-(4,4'-dimethoxytrityl)thymidine.

5'-(4,4'-Dimethoxytrityl)-3',3'-oxomethylenethymidine is added to a 0.5 M ammonia solution in dioxane. The resulting reaction mixture is stirred at room temperature overnight, ammonia and solvent evaporated, and the residue is chromatographed on silica.

Example 9.

Preparation of 5'-(4,4'-dimethoxytrityl)-3'-hydroxymethyl branched thymidine.

5'-(4,4'-Dimethoxytrityl)-3',3'-oxomethylenethymidine is added to an aqueous dioxane solution of sodium hydroxide at −10° C. The resulting reaction mixture is stirred at room temperature for 2 h, diluted with water under cooling, extracted with chloroform. The crude product is purified by chromatography on silica.

Example 10.

Preparation of 5'-(4,4'-dimethoxytrityl)-3'-methoxymethyl branched thymidine.

5'-(4,4'-Dimethoxytrityl)-3',3'-oxomethylenethymidine in methanol is added to a solution of sodium meoxide in methanol at −20° C. The solution stands at room temperature for 2 h, diluted with water under cooling, extracted with dichloromethane. The residue is chromatographed on silica.

Example 11.

Preparation of 5'-(4,4'-dimethoxytrityl)-3'-thiomethyl branched thymidine.

5'-(4,4'-Dimethoxytrityl)-3',3'-oxomethylenethymidine is added to a solution of sodium hydrogen sulfide (1.5 equivalent) in ethanol. The resulting reaction mixture is refluxed for 2 h. Ethanol is evaporated and the residue dissolved in chloroform, washed with brine. The crude product is purified by chromatography.

Example 12.

Preparation of 5'-(4,4'-dimethoxytrityl)-3'-methylthiomethyl branched thymidine.

5'-(4,4'-Dimethoxytrityl)-3',3'-oxomethylenethymidine is added to a solution of sodium thiomethoxide (1.0 equivalent) in ethanol. The resulting solution is refluxed for 1 hour. Ethanol is evaporated and the residue dissolved in water, extracted with chloroform. The crude product is purified by chromatography on silica.

Example 13.

Preparation of 5'-(4,4'-dimethoxytrityl)-3'-nitroethyl branched thymidine.

5'-(4,4'-Dimethoxytrityl)-3',3'-oxomethylenethymidine is added to a solution of nitromethane (1.5 equivalents) and triethylamine (5.0 equivalents) in dichloromethane. The resulting solution stands at room temperature overnight and the solvent evaporated. The crude product is purified by chromatography.

Example 14.

Preparation of 3'-aminoethyl branched 5'-(4,4'-dimethoxytrityl)thymidine.

5'-(4,4'-Dimethoxytrityl)-3'-nitroethyl branched thymidine (1.0 mmol) is added to a stirred suspension of sodium borohydride (2.0 mmol) and 10% palladium on charcoal in water at 0° C. The resulting reaction mixture is stirred for 1 h at room temperature, the solid filtered and the filtrate extracted with chloroform. The crude product is purified by chromatography.

Similarly, the following compounds are prepared:

1) 5'-(4,4'-dimethoxytrityl)-5-p-methoxybenzyl-3'-(p-aminophenoxymethyl) branched thymidine from 5'-(4,4'-dimethoxytrityl)-5-p-methoxybenzyl-3'-(p-nitrophenoxymethyl)thymidine.

2) 5'-(4,4'-dimethoxytrityl)-5-p-methoxybenzyl-3'-(4-aminobutoxymethyl) branched thymidine from 5'-(4,4'-dimethoxytrityl)-5-p-methoxybenzyl-3'-(4-nitrobutoxymethyl)thymidine.

3) 3'-t-Butyldimethylsilyl-5'-dimethoxytrityl-4'-aminomethyl thymidine from 3'-t-butyldimethylsilyl-5'-(4,4'-dimethoxytrityl)-4'-nitromethyl thymidine.

4) 3'-t-Butyldimethylsilyl-5'-(4,4'-dimethoxytrityl)-1'-aminomethyl thymidine from 1'-nitromethyl-3'-t-butyldimethylsilyl-5'-(4,4'-dimethoxytrityl)thymidine.

5) 3'-t-Butyldimethylsilyl-5'-dimethoxytrityl-4'-(2-aminoethyl)thymidine from 3'-t-butyldimethylsilyl-5'-dimethoxytrityl-4'-nitroethyl thymidine 6) 3'-t-Butyldimethylsilyl-5'-(4,4'-dimethoxytrityl)-1'-(2-aminoethyl)thymidine from 1'-nitroethyl-3'-t-butyldimethylsilyl-5'-(4,4'-dimethoxytrityl)thymidine.

7) 3'-t-Butyldimethylsilyl-5-p-methoxybenzyl-5'-dimethoxytrityl-4'-(4-aminobutoxymethyl)thymidine from 3'-t-butyldimethylsilyl-5-p-methoxybenzyl-5'-dimethoxytrityl-4'-(4-nitrobutoxymethyl)thymidine.

8) 3'-t-butyldimethylsilyl-5-p-methoxybenzyl-5'-dimethoxytrityl-4'-(p-aminophenoxymethyl) thymidine from 3'-t-butyldimethylsilyl-5-p-methoxybenzyl-5'-dimethoxytrityl-4'-(p-nitrophenoxymethyl) thymidine 9) 3'-t-Butyldimethylsilyl-5'-dimethoxytrityl-5-methoxybenzyl-1'-(4-aminobutoxymethyl)thymidine from 3'-t-Butyldimethylsilyl-5'-dimethoxytrityl-5-methoxybenzyl-1'-(4-nitrobutoxymethyl)thymidine 10) 3'-t-Butyldimethylsilyl-5'-dimethoxytrityl-5-methoxybenzyl-1'-(p-aminophenoxymethyl)thymidine from 3'-t-butyldimethylsilyl-5'-dimethoxytrityl-5-methoxybenzyl-1'-(p-nitrophenoxymethyl)thymidine.

11) 5'-(4,4'-Dimethoxytrityl)-3'-aminomethyl branched thymidine from 5'-(4,4'-dimethoxytrityl)-3'-nitromethyl branched thymidine.

12) 3'-t-Butyldimethylsilyl-5'-aminomethyl branched thymidine from 3'-t-butyldimethylsilyl-5'-nitromethyl branched thymidine.

Example 15.

Preparation of 5'-(4,4'-dimethoxytrityl)-3'-trifluoroacetamidoethyl branched thymidine 3'-Aminoethyl branched 5'-(4,4'-dimethoxytrityl) thymidine is added to a solution of ethyl thiotrifluoroacetate in THF. The resulting solution stands at room temperature for 6 h and the solvent evaporated. The crude product is purified by chromatography.

Similarly, the following compounds are prepared:

1) 5'-(4,4'-Dimethoxytrityl)-3'-trifluoroacetamidolmethyl branched thymidine from 3'-aminomethyl branched 5'-(4,4'-dimethoxytrityl)thymidine.

2) 5'-(4,4'-dimethoxytrityl)-5-p-methoxybenzyl-3'-(p-trifluoroacetamidophenoxymethyl) branched thymidine from 5'-(4,4'-dimethoxytrityl)-5-p-methoxybenzyl-3'-(p-aminophenoxymethyl)thymidine.

3) 5'-(4,4'-Dimethoxytrityl)-5-p-methoxybenzyl-3'-(4-trifluoroacetamidobutoxymethyl) branched thymidine from 5'-(4,4'-dimethoxytrityl)-5-p-methoxybenzyl-3'-(4-aminobutoxymethyl)thymidine.

4) 3'-t-Butyldimethylsilyl-5'-dimethoxytrityl-4'-trifluoroacetamidomethyl thymidine from 3'-t-butyldimethylsilyl-5'-(4,4'-dimethoxytrityl)-4'-aminomethyl thymidine.

5) 3'-t-Butyldimethylsilyl-5'-(4,4'-dimethoxytrityl)-1'-trifluoroacetamidomethyl thymidine from 1'-aminomethyl-3'-t-butyldimethylsilyl-5'-(4,4'-dimethoxytrityl)thymidine.

6) 3'-t-Butyldimethylsilyl-5'-dimethoxytrityl-4'-(2-trifluoroaceatmidoethyl)thymidine from 3'-t-butyldimethylsilyl-5'-dimethoxytrityl-4'-aminoethyl thymidine 7) 3'-t-Butyldimethylsilyl-5'-(4,4'-dimethoxytrityl)-1'-(2-trifluoroaceatmidoethyl)thymidine from 1'-aminoethyl-3'-t-butyldimethylsilyl-5'-(4,4'-dimethoxytrityl)thymidine.

8) 3'-t-Butyldimethylsilyl-5-p-methoxybenzyl-5'-dimethoxytrityl-4'-(4-trifluoroaceatmidobutoxymethyl) thymidine from 3'-t-butyldimethylsilyl-5-p-methoxybenzyl-5'-dimethoxytrityl-4'-(4-aminobutoxymethyl)thymidine.

9) 3'-t-Butyldimethylsilyl-5-p-methoxybenzyl-5'-dimethoxytrityl-4'-(p-trifluoroacetamidophenoxymethyl) thymidine from 3'-t-butyldimethylsilyl-5-p-methoxybenzyl-5'-dimethoxytrityl-4'-(p-aminophenoxymethyl) thymidine 10) 3'-t-Butyldimethylsilyl-5'-dimethoxytrityl-5-methoxybenzyl-1'-(4-trifluoroacetamidobutoxymethyl) thymidine from 3'-t-Butyldimethylsilyl-5'-dimethoxytrityl-5-methoxybenzyl-1'-(4-aminobutoxymethyl)thymidine 11) 3'-t-Butyldimethylsilyl-5'-dimethoxytrityl-5-methoxybenzyl-1'-(p-trifluoroacetamidophenoxymethyl) thymidine from 3'-t-butyldimethylsilyl-5'-dimethoxyotrityl-5-methoxybenzyl-1'-(p-aminophenoxymethyl)thymidine.

12) 3'-t-Butyldimethylsilyl-5'-trifluoroacetamidomethyl branched thymidine from 3'-t-butyldimethylsilyl-5'-aminomethyl branched thymidine.

13) 3'-t-Butyldimethylsilyl-5'-trifluoroacetamidoethyl branched thymidine from 3'-t-butyldimethylsilyl-5'-aminoethyl branched thymidine.

14) 3'-t-Butyldimethylsilyl-5'-trifluoroacetamidobutoxymethyl branched thymidine from 3'-t-butyldimethylsilyl-5'-aminobutoxymethyl branched thymidine.

15) 3'-t-Butyldimethylsilyl-5'-trifluoroacetamidophenoxymethyl branched thymidine from 3'-t-butyldimethylsilyl-5'-aminophenoxymethyl branched thymidine.

Example 16.

Preparation of 3'-acetoxymethyl branched 5'-(4,4'-dimethoxytrityl)thymidine.

5'-(4,4'-Dimethoxytrityl)-3'-hydroxymethyl branched thymidine is added to a mixture of acetic anhydride and pyridine. The solution stands at room temperature for 6 h, poured onto ice, extracted with dicloromethane. The crude product is purified by chromatography.

Similarly, the following compounds are prepared:

1) 3'-Acetylthiomethyl branched 5'-(4,4'-dimethoxytrityl) thymidine from 5'-(4,4'-dimethoxytrityl)-3'-thiomethyl branched thymidine.

2) 3'-t-Butyldimethylsilyl-5'-(4,4'-dimethoxytrityl)-1'-acetoxymethyl thymidine from 3'-t-butyldimethylsilyl-5'-(4,4'-dimethoxytrityl)-1'-hydroxymethyl thymidine.

3) 4'-Acetoxymethyl-3'-t-butyldimethylsilyl-5'-dimethoxytrityl thymidine from 3'-t-Butyldimethylsilyl-5'-dimethoxytrityl-4'-hydroxymethyl thymidine.

4) 5'-Acetoxymethyl branched 3'-t-butyldimethylsilyl-5'-dimethoxytrityl thymidine from 3'-t-Butyldimethylsilyl-5'-dimethoxytrityl-5"-hydroxymethyl branched thymidine.

Example 17

Preparation of 5'-(4,4'-dimethoxytrityl)-5-(t-butyldimethylsiloxymethyl)-3',3'-oxomethylene thymidine.

5'-(4,4'-Dimethoxytrityl)-3',3-oxomethylene thymidine in anhydrous dicholoromethane is added to a solution of t-butyldimethylsiloxymethyl chloride (3.0 equivalents) and triethylamine (5.0 equivalents) in dichloromethane. The reaction mixture is stirred at room temperature for 36 hours. Solvent is evaporated and extracted with ethyl acetate. The crude product is purified by chromatography.

Similarly, the following compounds are prepared:

1) 3'-t-Butyldimethylsilyl-5-(t-butyldimethylsiloxymethyl)-4"-bromomethyl-4'-formyl thymidine from 3'-t-butyldimethylsilyl-4"-bromomethyl-4'-formyl thymidine.

2) 3'-t-Butyldimethylsily-5-(t-butyldimethylsiloxymethyl)-4'-formyl thymidine from 3'-t-butyldimethylsilyl-4'-formyl thymidine.

3) 3'-t-Butyldimethylsilyl-1'-cyano-5'-(4,4'-dimethoxytrityl)-5-methoxybenzyl thymidine from 3'-t-butyldimethylsilyl-1'-cyano-5'-dimethoxytrityl thymidine.

4) 3',5,5'-Tris(methoxybenzyl)-1'-cyano-thymidine from 1'-cyanothymidine.

5) 3'-t-Butyldimethylsily-5-(t-butyldimethylsiloxymethyl)-5'-bromomethyl branched thymidine from 3'-t-Butyldimethylsily-5'-bromomethyl branched thymidine.

Example 18

Preparation of 5'-(4,4'-dimethoxytrityl)-5-(t-butyldimethylsiloxymethyl)-3'-ethyl branched thymidine.

5'-(4,4'-dimethoxytrityl)-5-(t-butyldimethylsiloxymethyl)-3',3-oxomethylene thymidine (1.0 mmol) dissolved in anhydrous THF is added to a stirred solution of lithium methyl cuprate (2.0 mmol) prepared from methyl lithium and cuprous cyanide in THF at −20° C. The resulting solution is stirred at this temperature for 2 h, quenched with ammonium chloride aqueous solution, stirred at room temperature for 30 min, and extracted with dichloromethane. The crude product is purified by chromatography.

Similarly, the following compounds are prepared:

1) 5'-(4,4'-Dimethoxytrityl)-5-(t-butyldimethylsiloxymethyl)-3'-propyl branched thymidine from 5'-(4,4'-dimethoxytrityl)-5-(t-butyldimethylsiloxymethyl)-3'-oxomethylene and lithium ethyl cuprate.

2) 5'-(4,4'-dimethoxytrityl)-5-(t-butyldimethylsiloxymethyl)-3'-benzyl branched thymidine from 5'-(4,4'-dimethoxytrityl)-5-(t-butyldimethylsiloxymethyl)-3'-oxomethylene thymidine and lithium phenyl cuprate.

Example 19

Preparation of 5'-(4,4'-dimethoxytrityl)-5-(t-butyldimethylsiloxymethyl)-3'-(2-nitroethoxymethyl) branched thymidine.

5'-(4,4'-Dimethoxytrityl)-5-(t-butyldimethylsiloxymethyl)-3',3'-oxomethylene thymidine in anhydrous THF is added dropwise to a stirred mixture of sodium hydride (1.0 equivalent) and nitroethanol (1.0 equivalent) at 0° C. The reaction mixture is stirred at room temperature for 2 h, quenched with water, and extracted with dichloromethane. The crude product is purified by chromatography.

Similarly, the following compounds are prepared:

1) 5'-(4,4'-dimethoxytrityl)-5-(t-butyldimethylsiloxymethyl)-3'-(p-nitrophenoxymethyl) branched thymidine from 5'-(4,4'-dimethoxytrityl)-5-(t-butyldimethylsiloxymethyl)-3'-oxomethylene thymidine and p-nitrophenol.

2) 5'(4,4'-dimethoxytrityl)-5-(t-butyldimethylsiloxymethyl)-3'-(4-nitrobutoxymethyl) branched thymidine from 5'-(4,4'-dimethoxytrityl)-5-(t-butyldimethylsiloxymethyl)-3'-oxomethylene thymidine and 4-nitrobutanol-1.

Example 20

Preparation of 5'-(4,4'-dimethoxytrityl)-3'-(2-nitroethoxymethyl) branched thymidine.

The deprotection procedure is similar to that for removal of TBDMS. A solution of 5'-(4,4'-dimethoxytrityl)-5-(t-butyldimethylsiloxymethyl)-3'-(2-nitroethoxymeyl) branched thymidine and tetrabutyl ammonium fluoride (4.0 equivalents) in THF stands at room temperature for 1 hour, poured into ice-water, extracted with dichloromethane. The extracts are washed with brine. The crude product is purified by chromatography.

Similarly, the following compounds are prepared:

1) 5'-(4,4'-Dimethoxytrityl)-3'-(2-nitroethyl) branched thymidine from 5'-(4,4'-dimethoxytrityl)-5-(t-butyldimethylsiloxymethyl)-3'-(2-nitroethyl) branched thymidine.

2) 5'-(4,4'-Dimethoxytrityl)-3'-(4-nitrobutoxymethyl) branched thymidine from 5'-(4,4'-dimethoxytrityl)-5-(t-butyldimethylsiloxymethyl)-3'-(4-nitrobutoxymethyl) branched thymidine.

3) 5'-(4,4'-Dimethoxytrityl)-3'-(p-nitrophenoxymethyl) branched thymidine from 5'-(4,4'-dimethoxytrityl)-5-(t-butyldimethylsiloxymethyl)-3'-(p-nitrophenoxymethyl) branched thymidine.

4) 5'-(4,4'-Dimethoxytrityl)-3'-(m-Aminobenzyl) branched thymidine from 5'-(4,4'-dimethoxytrityl)-5-(t-butyldimethylsiloxymethyl)-3'-(3-aminobenzyl) branched thymidine.

5) 3'-t-Butyldimethylsily-5'-cyanomethyl branched thymidine.

6) 3'-t-Butyldimethylsily-5'-cyanobutyl branched thymidine.

7) 3'-t-Butyldimethylsily-5'-nitrobutoxymethyl branched thymidine.

8) 3'-t-Butyldimethylsily-5'-nitrophenoxymethyl branched thymidine.

9) 3'-t-Butyldimethylsily-5'-cyanobenzyl branched thymidine.

Example 21

Preparation of phosphoramidite of 5'-(4,4'-dimethoxytrityl)-3'-trifluoroacetamidolmethyl branched thymidine.

To a stirred solution of 5'-(4,4'-dimethoxytrityl)-3'-trifluoroacetamidolmethyl branched thymidine and diisopropylethylamine (4.0 equivalents) in anhydrous dichloromethane is added 2-cyanoethyl-N,N-diisopropylchlorophosphoramidite (2.0 equivalents) in dichloromethane at 0° C. The resulting solution is stirred at room temperature for 1 h, diluted with dichloromethane under cooling, washed with cold 5% sodium bicarbonate and brine. The crude product is purified by chromatography on silica.

Similarly, the following compounds are prepared:

1) Phosphoramidite of 3'-Trifluoroacetamidoethyl branched 5'-(4,4'-dimethoxytrityl)thymidine.

2) Phosphoramidite of 5'-(4,4'-dimethoxytrityl)-5-(t-butyldimethylsiloxymethyl)-3'-(p-trifluoroacetamidophenoxymethyl) branched thymidine.

3) Phosphoramidite of 5'-(4,4'-dimethoxytrityl)-5-(t-butyldimethylsiloxymethyl)-3'-(4-trifluoroacetamidobutoxymethyl) branched thymidine.

4) Phosphoramidite of 5'-dimethoxytrityl-4'-trifluoroacetamidomethyl thymidine.

5) Phosphoramidite of 5'-(4,4'-dimethoxytrityl)-1'-trifluoroacetamidomethyl thymidine.

6) Phosphoramidite of 5'-dimethoxytrityl-4'-(2-trifluoroaceatmidoethyl)thymidine.

7) Phosphoramidite of 5'-(4,4'-dimethoxytrityl)-1'-(2-trifluoroaceatmidoethyl)thymidine.

8) Phosphoramidite of 5'-dimethoxytrityl-4'-(4-trifluoroaceatmidobutoxymethyl)thymidine.

9) Phosphoramidite of 5'-dimethoxytrityl-4'-(p-trifluoroacetamidophenoxymethyl)thymidine.

10) Phosphoramidite of 5'-dimethoxytrityl-1'-(4-trifluoroacetamidobutoxymethyl)thymidine.

11) Phosphoramidite of 5'-dimethoxytrityl-1'-(p-trifluoroacetamidophenoxymethyl)thymidine.

12) Phosphoramidite of 5'-dimethoxytrityl-5'-trifluoroacetamidomethyl branched thymidine.

13) 3'-t-Butyldimethylsilyl-5'-trifluoroacetamidoethyl branched thymidine from 3'-t-butyldimethylsilyl-5'-aminoethyl branched thymidine.

14) 3'-t-Butyldimethylsilyl-5'-trifluoroacetamidobutoxymethyl branched thymidine from 3'-t-butyldimethylsilyl-5'-aminobutoxymethyl branched thymidine.

15) 3'-t-Butyldimethylsilyl-5'-trifluoroacetamidophenoxymethyl branched thymidine from 3'-t-butyldimethylsilyl-5'-aminophenoxymethyl branched thymidine.

Example 22

Preparation of 3'-t-butyldimethylsilyl-4'-formyl thymidine.

3'-t-Butyldimethylsilyl thymidine is prepared as described in a published paper (O-Yang C., Wu, H. Y., Fraser-Smith E. B., Walker, K. A. M., *Tetrahedron Lett.* 1992, 33, 37–40). To a stirred mixture of 3'-t-butyldimethylsilyl thymidine, dicyclohexylcarbodiimide (3.0 equivalents), and Pyridine (1.0 equivalent) in anhydrous DMSO is added trifluoroacetic acid (0.5 equivalent) in DMSO at 0° C. and the resulting reaction mixture is stirred at room temperature overnight. Water (10 equivalents) is added and the mixture stirred for 1 h at room temperature. Precipitates are filtered and washed with a small amount of DMSO. The combined DMSO solution is diluted with chloroform, washed with brine for 5 times. The crude product is purified by chromatography on silica.

Example 23

Preparation of 3'-t-butyldimethylsily-5'-cyano branched thymidine.

To a stirred reaction mixture of 3'-t-butyldimethylsilyl-4'-formyl thymidine and sodium cyanide (1.0 equivalent) in DMF and water is added a saturated solution of sodium bisulfate at 0° C. The resulting reaction mixture is stirred at room temperature for 1 h, diluted with water, extracted with chloroform. The combined chloroform solution is washed with brine. The crude contains two diastereomers which are separated by chromatography on silica.

Example 24

Preparation of 3'-t-Butyldimethylsily-5'-nitro branched thymidine.

A reaction mixture of 3'-t-butyldimethylsilyl-4'-formyl thymidine and sodium nitrite (2.0 equivalents) in methyl sulfoxide is stirred at 50° C. overnight, diluted with chloroform, washed with brine. The crude contains two diastereomers which are separated by chromatography.

Example 25

Preparation of 3'-t-butyldimethylsilyl-5'-nitromethyl branched thymidine.

The preparation procedure is similar to that in a published paper (a. Tipson and Townsend "*Nucleic Acid Chemistry*", p521–526; b. Kappler, F., Hampton, A., *J. Org. Chem.*, 1975, 40, 1378). A solution of 3'-t-butyldimethylsilyl-4'-formyl thymidine, nitromethane (2.0 equivalents), and triethylamine (3.0 equivalents) in dichloromethane stands at room temperature overnight. Solvent is evaporated and the residue chromatographed on silica to give two diastereomers.

Example 26

3'-t-Butyldimethylsily-5-(t-butyldimethylsiloxymethyl)-5'-Methyl branched thymidine.

A solution of 3'-t-butyldimethylsilyl-5-methoxybenzyl-4'-formyl thymidine is added to a stirred solution of lithium methyl cuprate in anhydrous THF at −10° C. under nitrogen atmosphere. The reaction mixture is stirred for 2 h at room temperature and quenched with ammonium chloride aqueous solution. The mixture is extracted with dichloromethane and the crude product is purified by chromatography to give two diastereomers.

Similarly, the following compounds are prepared:

1) 3'-t-Butyldimethylsily-5-(t-butyldimethylsiloxymethyl)-5'-butyl branched thymidine from 3'-t-Butyldimethylsily-5-(t-butyldimethylsiloxymethyl)-5'-formyl thymidine and lithium butyl cuprate.

2) 3'-t-Butyldimethylsily-5-(t-butyldimethylsiloxymethyl)-5'-phenyl branched thymidine from 3'-t-Butyldimethylsily-5-(t-butyldimethylsiloxymethyl)-5'-formyl thymidine and lithium phenyl cuprate.

3) 3'-t-Butyldimethylsily-5-(t-butyldimethylsiloxymethyl)-5'-benzyl branched thymidine from 3'-t-Butyldimethylsily-5-(t-butyldimethylsiloxymethyl)-5'-formyl thymidine and lithium benzyl cuprate.

Example 27

3'-t-Butyldimethylsily-5-(t-butyldimethylsiloxymethyl)-5'-ethoxycarbonylmethyl branched thymidine.

A solution of 3'-t-butyldimethylsilyl-4'-formyl thymidine is added to a stirred solution of ethoxycarbonylmethyl zinc bromide in anhydrous THF prepared from zinc and ethyl acetate at −10° C. under argon atmosphere. The reaction mixture is stirred at room temperature for 2 h and quenched with ammonium chloride solution. The mixture is extracted with dichloromethane. The crude product is purified by chromatography.

Similarly, the following compound is prepared:
1) 3'-t-Butyldimethylsily-5-(t-butyldimethylsiloxymethyl)-5'-ethoxycarbonylbutyl branched thymidine from 3'-t-butyldimethylsilyl-5'-formyl thymidine and organozinc reagent prepared from ethoxycarbonylbutyl iodide and zinc.

Example 28

3'-t-Butyldimethylsily-5-(t-butyldimethylsiloxymethyl)-5'-cyanomethyl branched thymidine.

A solution of 3'-t-butyldimethylsilyl-4'-formyl thymidine is added to a stirred solution of cyanomethyl cadmium bromide (Burkhardt, E. R., Rieke, R. D., *J. Org. Chem.* 1985, 50, 416) in anhydrous THF prepared from cadmium and acetonitrile at −10° C. under argon atmosphere. The reaction mixture is stirred at room temperature for 4 h and quenched with ammonium chloride aqueous solution. The mixture is extracted with dichloromethane and the crude purified by chromatography.

Similarly, the following compounds are prepared:
1) 3'-t-Butyldimethylsily-5-(t-butyldimethylsiloxymethyl)-5'-cyanobutyl branched thymidine from 3'-t-butyldimethylsilyl-4'-formyl-5-(t-butyldimethylsiloxymethyl) thymidine and cyanobutyl cadmium bromide.

2) 3'-t-Butyldimethylsily-5-(t-butyldimethylsiloxymethyl)-5'-nitrobutyl branched thymidine from 3'-t-butyldimethylsilyl-4'-formyl-5-(t-butyldimethylsiloxymethyl)thymidine and nitrobutyl cadmium bromide.

3) 3'-t-Butyldimethylsily-5-(t-butyldimethylsiloxymethyl)-5'-nitrophenylethyl branched thymidine from 3'-t-butyldimethylsilyl-4'-formyl-5-(t-butyldimethylsiloxymethyl) thymidine and nitrophenylethyl cadmium bromide.

4) 3'-t-Butyldimethylsily-5-(t-butyldimethylsiloxymethyl)-5'-cyanobenzyl branched thymidine from 3'-t-butyldimethylsilyl-4'-formyl-5-(t-butyldimethylsiloxymethyl) thymidine and cyanobenzyl cadmium bromide.

Example 29

Preparation of 3'-t-butyldimethylsilyl-4"-bromomethyl-4'-formyl thymidine.

A reaction mixture of 3'-t-Butyldimethylsilyl-4"-hydroxymethyl-4'-formyl thymidine prepared according to a known procedure (a. O-Yang C., wu, H. Y., Fraser-Smith., E. B., Walker, K. A. M. *Tetrahedron Lett.*, 1992, 33, 37–40; b. Jones, G. H., Taniguchi, M., Tegg, D., Moffatt, J. G. *J. Org. Chem.* 1979, 44, 1309–17), carbon tetrabromide (10 equivalents), triphenylphosphine (2.0 equivalents) in chloroform is refluxed for two days. Solvent is evaporated and the residue is chromatographed on silica.

Similarly, the following compound is prepared:
1) 1'-Bromomethyl-3'-t-butyldimethylsilyl-5'-(4,4'-dimethoxytrityl)-5-((t-butyldimethylsiloxymethyl)) thymidine from 3'-t-butyldimethylsilyl-1'-hydroxymethyl-5'-(4,4'-dimethoxytrityl)-5-((t-butyldimethylsiloxymethyl)) thymidine.

Example 30

Preparation of 3'-t-butyldimethylsilyl-4"-bromomethyl thymidine.

3'-t-Butyldimethylsilyl-4"-bromomethyl-4'-formyl thymidine (1.0 mmol) in ethanol is added dropwise to a sodium borohydride (0.5 mmol) aqueous solution in such a rate that reaction temperature does not exceed 20° C. After addition the reaction mixture is stirred at room temperature for 20 min and a dilute hydrochloric acid added under cooling until the mixture is neutral. The mixture is extracted with ethyl acetate and the residue is chromatographed on silica.

Similarly, the following compound is prepared:
1) 3'-t-Butyldimethylsilyl-5'-(4,4'-dimethoxytrityl)-1'-hydroxymethyl-5-((t-butyldimethylsiloxymethyl)) thymidine from 3'-t-butyldimethylsilyl-5'-(4,4'-dimethoxytrityl)-1'-formyl-5-((t-butyldimethylsiloxymethyl))thymidine.

Example 31

Preparation of 3'-t-butyldimethylsilyl-5'-dimethoxytrityl-4'-bromomethyl thymidine.

3'-t-Butyldimethylsilyl-4'-bromomethyl thymidine dissolved in anhydrous pyridine is added to a stirred cold solution of 4,4'-dimethoxytrityl chloride in pyridine. The resulting solution stands at room temperature overnight. Pyridine is evaporated and the residue chromatographed on silica gel.

Similarly, the following compounds are prepared:
1) 1'-Cyano-5'-(4,4'-dimethoxytrityl)thymidine from 1'-Cyanothymidine (Uteza, V., Chen, G-R., Tuoi, J. L. Q., Descotes, G., Fenet, G., and Grouiller, A. *Tetrahedron*, 1993, 49, 8579–8488).

Example 32

Preparation of 3'-t-butyldimethylsilyl-5'-dimethoxytrityl-4'-cyanomethyl thymidine.

A mixture of 3'-t-Butyldimethylsilyl-5'-dimethoxytrityl-4'-bromomethyl thymidine and sodium cyanide (1.2 equivalent) in DMSO is stirred at 60° C. overnight, diluted with chloroform, washed with brine. The crude product is purified by chromatography.

Similarly, the following compound is prepared:
1) 3'-t-Butyldimethylsilyl-1'-cyanomethyl-5'-(4,4'-dimethoxytrityl)thymidine from 1'-bromomethyl-3'-t-butyldimethylsilyl-5'-(4,4'-dimethoxytrityl)thymidine.

Example 33.

Preparation of 3'-t-Butyldimethylsilyl-5'-dimethoxytrityl-4'-nitromethyl thymidine.

A mixture of 3'-t-butyldimethylsilyl-5'-(4,4'-dimethoxytrityl)-4'-bromomethyl thymidine and sodium nitrite (2.0 equivalents) in DMSO is stirred at room temperature overnight, diluted with chloroform, washed with brine. The crude product is purified by chromatography on silica.

Similarly, the following compound is prepared:
1) 3'-t-Butyldimethylsilyl-5'-(4,4'-dimethoxytrityl)-1'-nitromethyl thymidine from 1'-bromomethyl-3'-t-butyldimethylsilyl-5'-(4,4'-dimethoxytrityl)thymidine.

Example 34.

Preparation of 3'-t-Butyldimethylsilyl-5'-dimethoxytrityl-4'-azidomethyl thymidine.

A mixture of 3'-t-Butyldimethylsilyl-5'-dimethoxytrityl-4'-bromomethyl thymidine, sodium azide (3.0 equivalents), and hexadecyltributylphosphouium bromide (0.1 equivalent) in acetonitrile/water is stirred at room temperature overnight. Acetonitrile is evaporated and the remaining mixture extracted with chloroform. The crude product is purified by chromatography on silica.
Similarly, the following compounds is prepared:

1) 1'-Azidomethyl-3'-t-Butyldimethylsilyl-5'-(4,4'-dimethoxytrityl)thymidine from 1'-bromomethyl-3'-t-butyldimethylsilyl-5'-(4,4'-dimethoxytrityl)thymidine.

Example 35.

Preparation of 3'-t-butyldimethylsilyl-5'-dimethoxytrityl-4'-aminomethyl thymidine.

A solution of 3'-t-Butyldimethylsilyl-5'-dimethoxytrityl-4'-bromomethyl thymidine and 0.5 M ammonia solution in dioxane is stirred at room temperature overnight. Ammonia and solvent are evaporated and the crude product is purified by chromatography on silica.
Similarly, the following compound is prepared:

1) 1'-Aminomethyl-3'-t-butyldimethylsilyl-5'-(4,4'-dimethoxytrityl)thymidine from 1'-bromomethyl-3'-t-butyldimethylsilyl-5'-(4,4'-dimethoxytrityl)thymidine.

Example 36.

Preparation of 3'-t-Butyldimethylsilyl-5'-dimethoxytrityl-4'-hydroxymethyl thymidine.

A solution of 3'-t-butyldimethylsilyl-5'-dimethoxytrityl-4'-bromomethyl thymidine in dioxane is added to an stirred aqueous dioxane solution of sodium hydroxide at 0° C. The resulting reaction mixture is stirred at room temperature for 1 hour, diluted with water, extracted with chloroform. The crude product is purified by chromatography.
Similarly, the following compound is prepared:

1) 1'-Hydroxymethyl-3'-t-butyldimethylsilyl-5'-(4,4'-dimethoxytrityl)thymidine from 1'-bromomethyl-3'-t-butyldimethylsilyl-5'-(4,4'-dimethoxytrityl)thymidine.

Example 37.

Preparation of 3'-t-butyldimethylsilyl-5'-dimethoxytrityl-4'-methoxymethyl thymidine.

3'-t-Butyldimethylsilyl-5'-dimethoxytrityl-4'-cbromomethyl thymidine dissolved in methanol is added to a stirred solution of sodium methoxide in methanol at 0° C. The resulting solution stands at room temperature for 1 h, diluted with water, extracted with dichloromethane. The crude product is purified by chromatography.
Similarly, the following compound is prepared:

1) 3'-t-Butyldimethylsilyl-5'-(4,4'-dimethoxytrityl)-1'-methoxymethyl thymidine from 1'-bromomethyl-3'-t-butyldimethylsilyl-5'-(4,4'-dimethoxytrityl)thymidine.

Example 38.

Preparation of 3'-t-butyldimethylsilyl-5'-dimethoxytrityl-4'-thiomethyl thymidine.

t-Butyldimethylsilyl-5'-dimethoxytrityl-4'-bromomethyl thymidine in ethanol is added to a stirred solution of sodium hydrogen sulfide (1.5 equivalent) in ethanol/water. The reaction mixture is refluxed for 2 h. Ethanol is evaporated and the remaining mixture extracted with ethyl acetate. The crude product is purified by chromatography.
Similarly, the following compound is prepared:

1) 3'-t-Butyldimethylsilyl-5'-(4,4'-dimethoxytrityl)-1'-thiomethyl thymidine from 1'-bromomethyl-3'-t-butyldimethylsilyl-5'-(4,4'-dimethoxytrityl)thymidine.

Example 39.

Preparation of 3'-t-butyldimethylsilyl-5'-dimethoxytrityl-4'-methylthiomethyl thymidine.

3'-t-Butyldimethylsilyl-5'-dimethoxytrityl-4'-bromomethyl thymidine in ethanol is added to a stirred solution of sodium thiomethoxide (1.0 equivalent) in ethanol at 0° C. The reaction mixture is refluxed for 1 hour. Ethanol is evaporated and the residue diluted in water, extracted with ethylacetate. The crude product is purified by chromatography.
Similarly, the following compound is prepared:

1) 3'-t-Butyldimethylsilyl-5'-(4,4'-dimethoxytrityl)-1'-methylthiomethyl thymidine from 1'-bromomethyl-3'-t-butyldimethylsilyl-5'-(4,4'-dimethoxytrityl)thymidine.

Example 40.

Preparation of 3'-t-butyldimethylsilyl-5'-dimethoxytrityl-4'-(2-nitroethyl)thymidine.

3'-t-Butyldimethylsilyl-5'-dimethoxytrityl-4'-bromomethyl thymidine in dichloromethane is added to a stirred solution of nitromethane (2.0 equivalents) and triethylamine (4.0 equivalents) in dichloromethane at 0° C. The resulting solution stand at room temperature overnight. The solvent is evaporated and the residue chromatographed on silica.
Similarly, the following compound is prepared:

1) 3'-t-Butyldimethylsilyl-5'-(4,4'-dimethoxytrityl)-1'-(2-nitroethyl)thymidine from 1'-bromomethyl-3'-t-butyldimethylsilyl-5'-(4,4'-dimethoxytrityl)thymidine.

Example 41.

Preparation of 3'-t-butyldimethylsilyl-5-(t-butyldimethylsiloxymethyl)-5'-dimethoxytrityl-4'-benzyl thymidine.

3'-t-Butyldimethylsilyl-5-(t-butyldimethylsiloxymethyl)-5'-dimethoxytrityl-4'-bromomethyl thymidine in anhydrous THF is added dropwise to a stirred solution of lithium phenyl cuprate (3.0 equivalents) in THF at −78° C. The reaction mixture is stirred at 0° C. for 3 h. Saturated ammonium chloride solution is added and the mixture is extracted with ethyl acetate. The crude product is purified by chromatography
Similarly, the following compounds are prepared:

1) 3'-t-butyldimethylsilyl-5-(t-butyldimethylsiloxymethyl)-5'-dimethoxytrityl-4'-ethyl thymidine from 3'-t-butyldimethylsilyl-5-(t-butyldimethylsiloxymethyl)-5'-dimethoxytrityl-4'-bromomethyl thymidine and lithium methyl cuprate.

2) 3'-t-Butyldimethylsilyl-5-(t-butyldimethylsiloxymethyl)-5'-dimethoxytrityl-4'-pentyl thymidine 3'-t-Butyldimethylsilyl-5-(t-butyldimethylsiloxymethyl)-5'-dimethoxytrityl-4'-bromomethyl thymidine and lithium butyl cuprate.

3) 1'-Benzyl-3'-t-butyldimethylsilyl-5-(t-butyldimethylsiloxymethyl)-5'-dimethoxytrityl thymidine from 1'-bromomethyl-3'-t-butyldimethylsilyl-5-(t-butyldimethylsiloxymethyl)-5'-dimethoxytrityl thymidine and lithium phenyl cuprate.

4) 3'-t-Butyldimethylsilyl-5'-dimethoxytrityl-5-methoxybenzyl-1'-pentyl thymidine from 3'-t-butyldimethylsilyl-1'-bromomethyl-5'-dimethoxytrityl 5-(t-butyldimethylsiloxymethyl) thymidine and lithium butyl cuprate.

5) 3'-t-butyldimethylsilyl-5'-dimethoxytrityl-1'-ethyl-5-methoxybenzyl thymidine from 3'-t-butyldimethylsilyl-1'-bromomethyl-5'-dimethoxytrityl (t-butyldimethylsiloxymethyl) thymidine and lithium methylcuprate.

Example 42.

Preparation of 3'-t-butyldimethylsilyl-5-(t-butyldimethylsiloxymethyl)-5'-dimethoxytrityl-4'-(4-nitrobutoxymethyl)thymidine.

3'-t-Butyldimethylsilyl-5-(t-butyldimethylsiloxymethyl)-5'-dimethoxytrityl-4'-bromomethyl thymidine in anhydrous THF is added dropwise to a stirred mixture of sodium hydride (1.0 equivalent) and 4-nitrobutanol in anhydrous THF at 0° C. The reaction mixture is stirred at 0° C. overnight. Water is added and the mixture extracted with ethyl acetate. The crude product is purified by chromatography.

Similarly, the following compounds are prepared:

1) 3'-t-Butyldimethylsilyl-5-(t-butyldimethylsiloxymethyl)-5'-dimethoxytrityl-4'-(p-nitrophenoxymethyl) thymidine from 3'-t-butyldimethylsilyl-5-(t-butyldimethylsiloxymethyl)-5'-dimethoxytrityl-4'-bromomethyl thymidine and p-nitrophenol.

2) 3'-t-butyldimethylsilyl-5-(t-butyldimethylsiloxymethyl)-5'-dimethoxytrityl-4'-(2-cyanoethoxymethyl)thymidine from 3'-t-butyldimethylsilyl-5-(t-butyldimethylsiloxymethyl)-5'-dimethoxytrityl-4'-bromomethyl thymidine and 2-cyanoethanol.

3) 3'-t-Butyldimethylsilyl-5'-dimethoxytrityl-5-methoxybenzyl-1'-(4-nitrobutoxymethyl)thymidine from 3'-t-butyldimethylsilyl-1'-bromomethyl-5'-dimethoxytrityl (t-butyldimethylsiloxymethyl) thymidine and 4-nitrobutanol-1.

4) 3'-t-Butyldimethylsilyl-5'-dimethoxytrityl-5-methoxybenzyl-1'-(p-nitrophenoxymethyl)thymidine from 3'-t-butyldimethylsilyl-1'-bromomethyl-5'-dimethoxytrityl (t-butyldimethylsiloxymethyl)thymidine and p-nitrophenol.

Example 43.

Preparation of 1'-cyano-3'-t-butyldimethylsilyl-5'-(4,4'-dimethoxytrityl)thymidine.

1'-Cyano-5'-(4,4'-dimethoxytrityl)thymidine in anhydrous pyridine is added to a stirred solution of t-butyldimethylchlorosilane (1.5 equivalents) and imidazole (3.0 equivalents) in anhydrous pyridine at 0° C. The resulting reaction mixture is stirred at room temperature overnight. Pyridine is evaporated and the residue dissolved in ethyl acetate, washed with brine. The crude product is directly used for the next reaction.

Example 44.

Preparation of 3'-t-butyldimethylsilyl-5'-dimethoxytrityl-1'-formyl-5-methoxybenzyl thymidine.

3'-t-Butyldimethylsilyl-1'-cyano-5'-dimethoxytrityl-5-(t-butyldimethylsiloxymethyl) thymidine (1.0 mmol) in THF is added to a stirred solution of lithium triethoxyaluminum hydride (2.0 mmol) in THF at −20° C. under nitrogen. The reaction mixture is stirred at 5°–10° C. for 1 h, quenched with ammonium chloride aqueous solution. The mixture is extracted with ethyl acetate and the crude chromatographed on silica.

Example 45.

Preparation of 1'-amido-3, 5'-bis(t-butyldimethylsilyl)-5-tbutyldimethylsiloxymethyl thymidine.

1'-cyano-3',5',5-tris(methoxybenzyl)thymidine is added to a stirred aqueous solution of 30% hydrogen peroxide and sodium carbonate at 0° C. The reaction mixture is stirred at room temperature for 2 h, diluted with water, neutralized with dilute hydrochloric acid, extracted with dichloromethane. The crude product is purified by chromatography.

Example 46.

Preparation of 1'-amino-3, 5'-bis(t-butyldimethylsilyl)-5-t-butyldimethylsiloxymethyl thymidine.

The preparation procedure is similar as in described in the literature (Radhakrishna, A. S., Parham, M. E., Riggs, R. M., and Loudon, G. M. *J. Org. Chem.* 1979, 44, 1746). 1'-amido-3',5'-bis(t-butyldimethylsilyl)-5-t-butyldimethylsiloxymethyl thymidine (1.0 mmol) in anhydrous THF is added to a stirred solution of I,I-bis(trifluoroacetoxy)iodobenzene (2.0 mmol) in THF at 0° C. The reaction mixture is stirred at room temperature for 5 h, diluted with dichloromethane, washed with 5% sodium carbonate and brine. The crude product is purified by chromatography.

Example 47.

Preparation of trimethyl-3',5'-bis(t-butyldimethylsilyl)-5-t-butyldimethylsiloxymethylthymidin-1'-yl ammonium bromide.

1'-Amino-3',5'-bis(t-butyldimethylsilyl)-5-t-butyldimethylsiloxymethyl thymidine is added to a stirred solution of methyl bromide (10 equivalents) in THF at 0° C. The reaction mixture is stirred at 50° C. overnight. The solvent is evaporated and the crude product is purified by recrystallization.

Example 48.

Preparation of 1'-bromo-3',5'-bis(t-butyldimethylsilyl)-5-t-butyldimethylsiloxymethyl thymidine.

The procedure is similar as in the literature (Deady, L. W., Korytsky, O. L. *Tetrahedron Lett.* 1979, 451). Trimethyl-3', 5'-bis(t-butyldimethylsilyl)-5-t-butyldimethylsiloxymethyl thymidin-1-yl ammonium bromide is heated at 150° C. under vacuum overnight. The resulting product is used directly for next reaction.

Example 49.

Preparation of 1'-ethoxy-3',5'-bis(t-butyldimethylsilyl)-5-t-butyldimethylsiloxymethyl thymidine.

1'-bromo-3'3',5'-bis(t-butyldimethylsilyl)-5-t-butyldimethylsiloxymethyl thymidine in ethanol is added to a stirred solution of sodium ethoxide in ethanol at −10° C. The resulting reaction mixture is stirred at room temperature for 1 h, neutralized with dilute hydrochloric acid. Ethanol is evaporated and the remaining mixture extracted with ethyl acetate. The crude product is purified by chromatography to give a mixture of α and β diastereomers.

Similarly, the following compounds are prepared:

1) 1'-(4-nitrobutoxy)-3',5'-bis(t-butyldimethylsilyl)-5-t-butyldimethylsiloxymethyl thymidine from 1'-bromo-3'.5'-bis(t-butyldimethylsilyl)-5-t-butyldimethylsiloxymethyl thymidine and 4-nitributanol-1.

2) 1'-Ethylthio-3',5'-bis(t-butyldimethylsilyl)-5-t-butyldimethylsiloxymethyl thymidine from 1'-bromo-3',5'-bis(t-butyldimethylsilyl)-5-t-butyldimethylsiloxymethyl thymidine and sodium thioethoxide.

Example 50.

Preparation of 1'-amino-thymidine.

A suspension of 1'-amino-3',5'-bis(t-butyldimethylsilyl)-5-t-butyldimethylsiloxymethyl thymidine and tetrabutylammonium fluoride in THF stands at room temperature for one hour. The solvent is evaporated and the residue chromatographically separated on silica.

Example 51.

Preparation of an oligonucleotide containing the sugar modified nucleosides by phosphoramidite chemistry.

This example illustrates the use of Compound 6 (R=trifluoroacetamidoethyl) (REACTION SCHEME 1) for the synthesis of an oligonucleotide having sequence:

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 18 base pairs
      ( B ) TYPE: nucleic acid
      ( C ) STRANDEDNESS: unknown
      ( D ) TOPOLOGY: unknown ( i i ) MOLECULE TYPE: DNA (other nucleic acid)

( x i ) SEQUENCE DESCRIPTION: SEQ ID NO:1:

TTCCTGTCTG ATGGCTTC                                             18

( 2 ) INFORMATION FOR SEQ ID NO:2:

( i ) SEQUENCE CHARACTERISTICS:
      ( A ) LENGTH: 18 base pairs
      ( B ) TYPE: nucleic acid
      ( C ) STRANDEDNESS: unknown
      ( D ) TOPOLOGY: unknown ( i i ) MOLECULE TYPE: DNA (other nucleic acid)

( x i ) SEQUENCE DESCRIPTION: SEQ ID NO:2:

ATCTCTCCGC TTCCTTTC                                             18

---

5'-d(TAGT*CT*GGT*ACGCAT)-3'

In this sequence A, C, G, and T represent the unmodified deoxyribonucleoside and T* represents a sugar modified nucleoside of the invention.

The oligonucleotide in this example is synthesized by an ABI 394 DNA Synthesizer. All the nucleosides are incorporated by using phosphoramidite chemistry. Incorporation of dA, dC, dG, and T is carried out by using the standard DNA synthesis reagents and the standard procedure. Because of the steric hindrance of branched substituent at C3' position of thymidine, incorporation of T* is carried out by using (1) (2) higher concentration of the phosphoramidite, i.e., up to 0.3 mmol, longer coupling time, i.e., up to 45 min, and (3) multiple couplings, i.e., up to four times. After the synthesis, the work-up of the synthesized oligonucleotide follows the standard procedure. The modified oligonucleotide is degraded by enzyme digestion using snake venom phosphodiesterase and bacterial alkaline phosphatase at 37° C. for 20 h.

INCORPORATION BY REFERENCE

All patents, patents applications, and publications cited herein are hereby incorporated by reference.

EQUIVALENTS

The foregoing written specification is considered to be sufficient to enable one skilled in the art to practice the invention. Indeed, various modifications of the above-described invention which are obvious to those skilled in the field of organic chemistry or related fields are intended to be within the scope of the following claims.

What is claimed is:

1. A nucleoside having the structure:

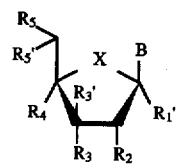

wherein:

$R_2$ is selected from the group consisting of H, OH, alkoxy, aralkoxy and aryloxy;

$R_3$ and $R_5$ are independently selected from the group consisting of OH, OCEPA and a hydroxyl bearing a blocking group;

X is selected from the group consisting of S and NH;

B is a modified or unmodified nucleoside base selected from the group consisting of Adenine, Guanine, Cytosine, Uracil and Thymine;

$R_1'$, $R_3'$, $R_4'$ and $R_5'$ are independently selected from the group consisting of H, alkyl, substituted alkyl, aralkyl, substituted aralkyl, aryl, and substituted aryl, provided that $R_1'$, $R_3'$, $R_4'$ and $R_5'$ cannot all be H at the same time;

wherein:

any alkyl portion of $R_1'$, $R_3'$, $R_4'$ and $R_5'$ is $C_1$ to $C_{10}$ linear or branched, saturated or unsaturated; the substituted portion of at least one of the substituted alkyl, substituted aralkyl and substituted aryl is selected from the group consisting of CN, $NO_2$, $N_3$, $CF_3$, $NH_2$, $NR_2$, OH, OR, SH, COOH, COOR, $SO_3R$, F, Cl, Br, and I, where R is selected from the group consisting of H, alkyl, aralkyl, aryl, Ac, $CF_3CO$, Ts; and any aryl portion of $R_1'$, $R_3'$, $R_4'$ and $R_5'$ is a phenyl, polycyclic ring or heterocycle.

2. The nucleoside of claim 1 wherein $R_1'$ is selected from the group consisting of alkyl, substituted alkyl, aralkyl, substituted aralkyl, aryl, and substituted aryl, and $R_3'$, $R_4'$ and $R_5'$ are all H.

3. The nucleoside of claim 1 wherein $R_3'$ is selected from the group consisting of alkyl, substituted alkyl, aralkyl, substituted aralkyl, aryl, and substituted aryl, and $R_1'$, $R_4'$ and $R_5'$ are all H.

4. The nucleoside of claim 1 wherein $R_4'$ is selected from the group consisting of alkyl, substituted alkyl, aralkyl, substituted aralkyl, aryl, and substituted aryl, and $R_1'$, $R_3'$ and $R_5'$ are all H.

5. The nucleoside of claim 1 wherein $R_5'$ is selected from the group consisting of alkyl, substituted alkyl, aralkyl, substituted aralkyl, aryl, and substituted aryl, and $R_1'$, $R_3'$ and $R_4'$ are all H.

6. An oligonucleotide containing the nucleoside of claim 1 wherein $R_1'$ is selected from the group consisting of alkyl, substituted alkyl, aralkyl, substituted aralkyl, aryl, and substituted aryl, and $R_3'$, $R_4'$ and $R_5'$ are all H.

7. An oligonucleotide containing the nucleoside of claim 1 wherein $R_3'$ is selected from the group consisting of alkyl, substituted alkyl, aralkyl, substituted aralkyl, aryl, and substituted aryl, and $R_1'$, $R_4'$ and $R_5'$ are all H.

8. An oligonucleotide containing the nucleoside of claim 1 wherein $R_4'$ is selected from the group consisting of alkyl, substituted alkyl, aralkyl, substituted aralkyl, aryl, and substituted aryl, and $R_1'$, $R_3'$ and $R_5'$ are all H.

9. An oligonucleotide containing the nucleoside of claim 1 wherein $R_5'$ is selected from the group consisting of alkyl, substituted alkyl, aralkyl, substituted aralkyl, aryl, and substituted aryl, and $R_1'$, $R_3'$ and $R_4'$ are all H.

* * * * *